(12) United States Patent
Dillmann et al.

(10) Patent No.: US 7,919,475 B2
(45) Date of Patent: Apr. 5, 2011

(54) COMPOSITIONS AND METHODS FOR IMPROVING HEART FUNCTION

(75) Inventors: Wolfgang Dillmann, Solana Beach, CA (US); Raymond Clark, San Marcos, CA (US)

(73) Assignee: The Regents of The University of California, Oakland, CA (US)

( * ) Notice: Subject to any disclaimer, the term of this patent is extended or adjusted under 35 U.S.C. 154(b) by 480 days.

(21) Appl. No.: 11/574,232

(22) PCT Filed: Aug. 25, 2005

(86) PCT No.: PCT/US2005/030504
§ 371 (c)(1),
(2), (4) Date: Jan. 30, 2008

(87) PCT Pub. No.: WO2006/026478
PCT Pub. Date: Mar. 9, 2006

(65) Prior Publication Data
US 2008/0313753 A1    Dec. 18, 2008

Related U.S. Application Data

(60) Provisional application No. 60/604,360, filed on Aug. 25, 2004.

(51) Int. Cl.
*A61K 48/00* (2006.01)
*A01N 63/00* (2006.01)
*C07H 21/02* (2006.01)
*C07H 21/04* (2006.01)

(52) U.S. Cl. .............. 514/44 R; 424/93.21; 435/325; 536/23.1; 536/23.2

(58) Field of Classification Search .............. 514/44; 424/93.21; 435/325; 536/23.1, 23.2
See application file for complete search history.

(56) References Cited

U.S. PATENT DOCUMENTS
2003/0175923 A1    9/2003 Tang et al.

OTHER PUBLICATIONS

Patil et al. The AAPS Journal, 7(1): Article 9, E61-E77, 2005.*
Kay et al. Nature Med., 7(1): 33-40, Jan. 2001.*
Sasano et al. J. of Mol. Cell. Cardiology, 42: 954-961, 2007.*
Trent. Chapter 6, Genetics and Cellular Therapies from Molecular Med: An Introductory Text, 2005, pp. 143-173.*
Zhao et al. Basic Res. Cardiol., 97:348-358, 2002.*
Ahmed, Am. Heart J. (1975) 89:153-158.
Chu et al., Circ. Res. (2004) 94(2):184-193.
Clark et al., Journal of Biological Chemistry (2003) 278:44230-44237.
Fein, Cir. Res. (1980) 47:922-933.
Galderisi, Am. J. Cardiol. (1991) 68:85-89.
Gupta, Biophys. J. (1993) 65:2547-2558.
Hu et al., Circ. Res. (2005) 96(9):925-926.
International Search Report for PCT/US05/30504, mailed on Apr. 28, 2006, 2 pages.
Li et al., Acta Pharmacologica Sinica (2005) 26:51-55.
Marshall, J. Biol. Chem. (1991) 266:4706-4712.
Parker, J. Biol. Chem. (2003) 278:10022-10027.
Penpargkul, J. Mol. Cell Cardiol. (1981) 13:303-309.
Ren, Am. J. Physiol. (1997) 273:H2876-2883.
Trost, Diabetes (2002) 51:1166-1171.
Vangheluwe et al., Biochem J. (2005) 389:151-159.
Vosseller, PNAS USA (2002) 99:5313-5318.
Zarich, J. Am. Coll. Cardiol. (1988) 12:114-120.

* cited by examiner

*Primary Examiner* — Thaian N Ton
(74) *Attorney, Agent, or Firm* — Gavrilovich, Dodd & Lindsey; Gregory P. Einhorn

(57) ABSTRACT

The present invention relates to treating or ameliorating heart disease associated with poor myocardial performance, e.g., diabetic cardiomyopathy and associated disorders, particularly to treating, preventing or ameliorating such disorders through inhibition of O-GlcNAcylation and/or increased activity of O-GlnNAcase. The invention provides vectors for gene transfer of O-GlnNAcase. In one aspect, the invention provides cells, vectors, formulations comprising them and methods of using them, for the gene transfer of the human O-GlnNAcase gene, e.g., to treat conditions and diseases associated with impaired cardiac contractility, such as that, found associated with diabetic cardiomyopathy. In another aspect, the invention provides non-human transgenic animals and host cells comprising genetically engineered cells having increased activity of O-GlnNAcase.

10 Claims, 18 Drawing Sheets

A

B

C

A

B

SEQUENCE LISTING

```
<160> NUMBER OF SEQ ID NOS: 1

<210> SEQ ID NO 1
<211> LENGTH: 1046
<212> TYPE: PRT
<213> ORGANISM: Artificial Sequence
<220> FEATURE:
<223> OTHER INFORMATION: Chemically engineered

<400> SEQUENCE: 1

Met Ala Ser Ser Val Gly Asn Val Ala Asp Ser Thr Glu Pro Thr Lys
```

```
          1               5                  10                 15
        Arg Met Leu Ser Phe Gln Gly Leu Ala Glu Leu Ala His Arg Glu Tyr
                         20                 25                 30

Gln Ala Gly Asp Phe Glu Ala Glu Arg His Cys Met Gln Leu Trp
                     35                 40                 45

Arg Gln Glu Pro Asp Asn Thr Gly Val Leu Leu Leu Ser Ser Ile
                     50                 55                 60

His Phe Gln Cys Arg Arg Leu Asp Arg Ser Ala His Phe Ser Thr Leu
         65                 70                 75                 80

Ala Ile Lys Gln Asn Pro Leu Leu Ala Glu Ala Tyr Ser Asn Leu Gly
                         85                 90                 95

Asn Val Tyr Lys Glu Arg Gly Gln Leu Gln Glu Ala Ile Glu His Tyr
                        100                105                110

Arg His Ala Leu Arg Leu Lys Pro Asp Phe Ile Asp Gly Tyr Ile Asn
                        115                120                125

Leu Ala Ala Ala Leu Val Ala Ala Gly Asp Met Glu Gly Ala Val Gln
                        130                135                140

Ala Tyr Val Ser Ala Leu Gln Tyr Asn Pro Asp Leu Tyr Cys Val Arg
        145                150                155                160

Ser Asp Leu Gly Asn Leu Leu Lys Ala Leu Gly Arg Leu Glu Glu Ala
                        165                170                175

Lys Ala Cys Tyr Leu Lys Ala Ile Glu Thr Gln Pro Asn Phe Ala Val
                        180                185                190

Ala Trp Ser Asn Leu Gly Cys Val Phe Asn Ala Gln Gly Glu Ile Trp
                        195                200                205

Leu Ala Ile His His Phe Glu Lys Ala Val Thr Leu Asp Pro Asn Phe
                        210                215                220

Leu Asp Ala Tyr Ile Asn Leu Gly Asn Val Leu Lys Glu Ala Arg Ile
        225                230                235                240

Phe Asp Arg Ala Val Ala Ala Tyr Leu Arg Ala Leu Ser Leu Ser Pro
                        245                250                255

Asn His Ala Val Val His Gly Asn Leu Ala Cys Val Tyr Tyr Glu Gln
                        260                265                270

Gly Leu Ile Asp Leu Ala Ile Asp Thr Tyr Arg Arg Ala Ile Glu Leu
                        275                280                285

Gln Pro His Phe Pro Asp Ala Tyr Cys Asn Leu Ala Asn Ala Leu Lys
                        290                295                300

Glu Lys Gly Ser Val Ala Glu Ala Glu Asp Cys Tyr Asn Thr Ala Leu
        305                310                315                320

Arg Leu Cys Pro Thr His Ala Asp Ser Leu Asn Asn Leu Ala Asn Ile
                        325                330                335

Lys Arg Glu Gln Gly Asn Ile Glu Glu Ala Val Arg Leu Tyr Arg Lys
                        340                345                350

Ala Leu Glu Val Phe Pro Glu Phe Ala Ala Ala His Ser Asn Leu Ala
                        355                360                365

Ser Val Leu Gln Gln Gln Gly Lys Leu Gln Glu Ala Leu Met His Tyr
                        370                375                380

Lys Glu Ala Ile Arg Ile Ser Pro Thr Phe Ala Asp Ala Tyr Ser Asn
        385                390                395                400

Met Gly Asn Thr Leu Lys Glu Met Gln Asp Val Gln Gly Ala Leu Gln
                        405                410                415

Cys Tyr Thr Arg Ala Ile Gln Ile Asn Pro Ala Phe Ala Asp Ala His
                        420                425                430
```

```
Ser Asn Leu Ala Ser Ile His Lys Asp Ser Gly Asn Ile Pro Glu Ala
        435                 440                 445

Ile Ala Ser Tyr Arg Thr Ala Leu Lys Leu Lys Pro Asp Phe Pro Asp
    450                 455                 460

Ala Tyr Cys Asn Leu Ala His Cys Leu Gln Ile Val Cys Asp Trp Thr
465                 470                 475                 480

Asp Tyr Asp Glu Arg Met Lys Lys Leu Val Ser Ile Val Ala Asp Gln
                485                 490                 495

Leu Glu Lys Asn Arg Leu Pro Ser Val His Pro His Ser Met Leu
            500                 505                 510

Tyr Pro Leu Ser His Gly Phe Arg Lys Ala Ile Ala Glu Arg His Gly
        515                 520                 525

Asn Leu Cys Leu Asp Lys Ile Asn Val Leu His Lys Pro Pro Tyr Glu
    530                 535                 540

His Pro Lys Asp Leu Lys Leu Ser Asp Gly Arg Leu Arg Val Gly Tyr
545                 550                 555                 560

Val Ser Ser Asp Phe Gly Asn His Pro Thr Ser His Leu Met Gln Ser
                565                 570                 575

Ile Pro Gly Met His Asn Pro Asp Lys Phe Glu Val Phe Cys Tyr Ala
        580                 585                 590

Leu Ser Pro Asp Asp Gly Thr Asn Phe Arg Val Lys Val Met Ala Glu
    595                 600                 605

Ala Asn His Phe Ile Asp Leu Ser Gln Ile Pro Cys Asn Gly Lys Ala
610                 615                 620

Ala Asp Arg Ile His Gln Asp Gly Ile His Ile Leu Val Asn Met Asn
625                 630                 635                 640

Gly Tyr Thr Lys Gly Ala Arg Asn Glu Leu Phe Ala Leu Arg Pro Ala
                645                 650                 655

Pro Ile Gln Ala Met Trp Leu Gly Tyr Pro Gly Thr Ser Gly Ala Leu
        660                 665                 670

Phe Met Asp Tyr Ile Ile Thr Asp Gln Glu Thr Ser Pro Ala Glu Val
    675                 680                 685

Ala Glu Gln Tyr Ser Glu Lys Leu Ala Tyr Met Pro His Thr Phe Phe
690                 695                 700

Ile Gly Asp His Ala Asn Met Phe Pro His Leu Lys Lys Lys Ala Val
705                 710                 715                 720

Ile Asp Phe Lys Ser Asn Gly His Ile Tyr Asp Asn Arg Ile Val Leu
                725                 730                 735

Asn Gly Ile Asp Leu Lys Ala Phe Leu Asp Ser Leu Pro Asp Val Lys
        740                 745                 750

Ile Val Lys Met Lys Cys Pro Asp Gly Gly Asp Asn Ala Asp Ser Ser
    755                 760                 765

Asn Thr Ala Leu Asn Met Pro Val Ile Pro Met Asn Thr Ile Ala Glu
770                 775                 780

Ala Val Ile Glu Met Ile Asn Arg Gly Gln Ile Gln Ile Thr Ile Asn
785                 790                 795                 800

Gly Phe Ser Ile Ser Asn Gly Leu Ala Thr Thr Gln Ile Asn Asn Lys
                805                 810                 815

Ala Ala Thr Gly Glu Glu Val Pro Arg Thr Ile Val Thr Thr Arg
        820                 825                 830

Ser Gln Tyr Gly Leu Pro Glu Asp Ala Ile Val Tyr Cys Asn Phe Asn
    835                 840                 845

Gln Leu Tyr Lys Ile Asp Pro Ser Thr Leu Gln Met Trp Ala Asn Ile
850                 855                 860
```

-continued

```
Leu Lys Arg Val Pro Asn Ser Val Leu Trp Leu Leu Arg Phe Pro Ala
865                 870                 875                 880

Val Gly Glu Pro Asn Ile Gln Gln Tyr Ala Gln Asn Met Gly Leu Pro
                885                 890                 895

Gln Asn Arg Ile Ile Phe Ser Pro Val Ala Pro Lys Glu Glu His Val
            900                 905                 910

Arg Arg Gly Gln Leu Ala Asp Val Cys Leu Asp Thr Pro Leu Cys Asn
            915                 920                 925

Gly His Thr Thr Gly Met Asp Val Leu Trp Ala Gly Thr Pro Met Val
    930                 935                 940

Thr Met Pro Gly Glu Thr Leu Ala Ser Arg Val Ala Ala Ser Gln Leu
945                 950                 955                 960

Thr Cys Leu Gly Cys Leu Glu Leu Ile Ala Lys Asn Arg Gln Glu Tyr
            965                 970                 975

Glu Asp Ile Ala Val Lys Leu Gly Thr Asp Leu Glu Tyr Leu Lys Lys
            980                 985                 990

Val Arg Gly Lys Val Trp Lys Gln Arg Ile Ser Ser Pro Leu Phe Asn
            995                 1000                1005

Thr Lys Gln Tyr Thr Met Glu Leu Glu Arg Leu Tyr Leu Gln Met Trp
    1010                1015                1020

Glu His Tyr Ala Ala Gly Asn Lys Pro Asp His Met Ile Lys Pro Val
1025                1030                1035                1040

Glu Val Thr Glu Ser Ala
                1045
```

COMPOSITIONS AND METHODS FOR IMPROVING HEART FUNCTION

FEDERAL FUNDING

This invention was made with government support under grant numbers HL66917, RO1 HL 66917 and RO1 HL 52946, awarded by the National Institutes of Health. The government has certain rights in the invention.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 220002067300seqlist.txt | Feb. 20, 2007 | 9,148 bytes |

TECHNICAL FIELD

This invention relates to molecular and cellular biology, biochemistry, molecular genetics, gene therapy, and pharmacology. The present invention relates to treating or ameliorating heart disease associated with poor myocardial performance, e.g., diabetic cardiomyopathy and associated disorders, particularly to treating, preventing or ameliorating such disorders through inhibition of O-GlcNAcylation by increasing the activity or levels of O-GlcNAcase (GCA), or decreasing levels of UDP-N-acetylglucosamine:peptide N-acetylglucosaminyl transferase (also called "O-linked GlcNAc transferase (O-GlcNAc, OGT) transferase", or "O-GlcNAc transferase" or "OGT"). The invention provides vectors for gene transfer of O-GlcNAcase (GCA). In one aspect, the invention provides cells, vectors, formulations comprising them and methods of using them, for the gene transfer of the human O-GlcNAcase gene, e.g., to treat conditions and diseases associated with impaired cardiac contractility, such as that found associated with diabetic cardiomyopathy. In another aspect, the invention provides non-human transgenic animals and host cells comprising genetically engineered cells having increased activity of O-GlcNAcase (GCA).

UDP-N-acetylglucosamine-peptide N-acetylglucosaminyltransferase 110 kDa subunit (EC 2.4.1.-) (O-GlcNAc (OGT) transferase p110 subunit) functions by the addition of nucleotide-activated sugars directly onto a polypeptide through O-glycosidic linkage with the hydroxyl of serine or threonine.

BACKGROUND

The leading cause of mortality among diabetic patients in the United States is heart disease. Despite the numerous effects diabetes exerts on the cardiovascular system, there is substantial evidence indicating that a diabetes-specific cardiomyopathy occurs in the absence of coronary artery disease or hypertension (see, e.g., Ahmed (1975) Am. Heart J. 89:153-158; Galderisi (1991) Am. J. Cardiol. 68:85-89). Diabetic cardiomyopathy is characterized by impaired cardiac contractility and poor myocardial performance without an attendant vascular or valvular disease and can lead to congestive heart failure. Studies in diabetic human patients and animal models have demonstrated the early development of diastolic dysfunction prior to the alteration of systolic function (see, e.g., Fein (1980) Cir. Res. 47:922-933, Zarich (1988) J. Am. Coll. Cardiol. 12:114-120). Eventually, however, nearly all aspects of cardiac contractility appear to become impaired (see, e.g., Trost (2002) Diabetes 51:1166-1171, Penpargkul (1981) J. Mol. Cell. Cardiol. 13:303-309). Abnormalities in cardiac $Ca^{2+}$ handling may be an important contributor to decreased contractile function in the diabetic heart.

Diabetic hyperglycemia results in a number of pathophysiological changes in the vascular system, but investigations of its role in diabetic cardiomyopathy are limited, but investigations of its role in diabetic cardiomyopathy are limited. Studies exposing cardiac myocytes to elevated extracellular glucose resulted in impaired cardiomyocytes contractility and calcium flux (see, e.g., Ren (1997) Am. J. Physiol. 273, H2876-2883) and increased $[Ca^{2+}]_i$ Gupta (1993) Biophys. J. 65:2547-2558). The observation that the diastolic dysfunction observed in myocytes exposed to elevated extracellular glucose could be duplicated by incubation of cardiomyocytes with glucosamine, a precursor to cellular N- and O-linked glycosylation, suggested that the mechanism may involve increased flux of glucose into the hexosamine pathway (Ren (1997) supra). Increased hexosamine flux is known to lead to insulin resistance in many tissues (see, e.g., Marshall (1991) J. Biol. Chem. 266:4706-4712), and recent studies indicate that dynamic O-GlcNAcylation (the dynamic addition and removal of a single O-linked N-acetylglucosamine residue) may prove to be an important player in diabetes (see, e.g., Vosseller (2002) Proc. Natl. Acad. Sci. USA 99:5313-5318; Parker (2003) J. Biol. Chem. 278:10022-10027.

SUMMARY

The present invention providing compositions and methods for treating or ameliorating heart disease associated with poor myocardial performance, e.g., diabetic cardiomyopathy and associated disorders. In one aspect, the invention provides compositions and methods for increasing O-GlcNAcase (GCA). activity in cells, e.g., myocytes (e.g., cardiomyocytes), in vivo, ex vivo or in vitro.

The invention provides vectors, expression cassettes and promoters for inserting a nucleic acid expressing an O-GlcNAcase (GCA) into a cell, e.g., as a gene transfer composition, and methods of using them, e.g., for gene therapy. In one aspect, the invention provides vectors, expression cassettes and promoters, formulations comprising them and methods of using them, for the gene transfer of the human O-GlcNAcase (GCA) gene or equivalent enzyme coding sequence (or sequences, if more than one isozyme is expressed at once), e.g., to treat, prevent or ameliorate heart disease associated with poor myocardial performance, e.g., diabetic cardiomyopathy and associated disorders. Exemplary vectors, expression cassettes and promoters are described herein.

In another aspect, the invention provides non-human transgenic animals and host cells comprising the O-GlcNAcase (GCA)-expressing vectors, expression cassettes and cells of the invention, as described herein. The invention provides non-human transgenic animals and host cells comprising the nucleic acid constructs of the invention, e.g., the vectors and promoters of the invention, and methods of using them. Also provided herein are animal cells (e.g., human cells) comprising the O-GlcNAcase (GCA) expressing nucleic acid constructs of the invention, e.g., the O-GlcNAcase (GCA) expressing vectors, expression cassettes and cells of the invention, e.g., as an episomal element, e.g., in an expression vector, or, as a heterologous insert stably inserted into the genome of the cell.

The invention provides methods for decreasing the calcium transient ($T_{1/2}$) intracellular calcium flux in a myocyte under hyperglycemic or diabetic conditions comprising (a) providing a nucleic acid encoding an O-GlcNAcase, wherein the nucleic acid is operatively linked to a promoter constitutively or inducibly active in the myocyte or the heart, or an O-GlcNAcase (GCA) protein; and (b) administering an effective amount of the nucleic acid or (GCA) protein to the myocyte, thereby decreasing the calcium transient ($T_{1/2}$).

The invention provides methods for ameliorating diastolic impairment in calcium flux in a diabetic heart comprising (a) providing a nucleic acid encoding an O-linked GlcNAc transferase (O-GlcNAc, OGT), wherein the nucleic acid is operatively linked to a promoter constitutively or inducibly active in the myocyte or the heart, or an O-GlcNAc (OGT) protein; and (b) administering an effective amount of the nucleic acid or OGT protein to the heart, thereby ameliorating diastolic impairment in calcium flux.

The invention provides methods for improving (normalizing) calcium cycling in a myocyte under hyperglycemic or diabetic conditions, or a diabetic heart, by enhancing the $Ca^{2+}$ transient and sarcoplasmic reticulum $Ca^{2+}$ loading, the method comprising (a) providing a nucleic acid encoding an O-linked GlcNAc transferase (O-GlcNAc, OGT), wherein the nucleic acid is operatively linked to a promoter constitutively or inducibly active in the myocyte or the heart, or an O-GlcNAc (OGT) protein; and (b) administering an effective amount of the nucleic acid or OGT protein to the myocyte or heart, thereby enhancing the $Ca^{2+}$ transient and sarcoplasmic reticulum $Ca^{2+}$ loading in the myocyte or heart.

The invention provides methods for lowering PLB expression in a myocyte under hyperglycemic or diabetic conditions, or in a diabetic heart, the method comprising (a) providing a nucleic acid encoding an O-linked GlcNAc transferase (O-GlcNAc, OGT), wherein the nucleic acid is operatively linked to a promoter constitutively or inducibly active in the myocyte or the heart, or an O-GlcNAc (OGT) protein; and (b) administering an effective amount of the nucleic acid or OGT protein to the myocyte or the heart, thereby lowering PLB expression in the myocyte or the heart.

The invention provides methods for increasing or normalizing SERCA2a expression, ERCA2a/PLB ratio and/or SERCA2a activity in a myocyte under hyperglycemic or diabetic conditions, or in a diabetic heart, the method comprising (a) providing a nucleic acid encoding an O-linked GlcNAc transferase (O-GlcNAc, OGT), wherein the nucleic acid is operatively linked to a promoter constitutively or inducibly active in the myocyte or the heart, or an O-GlcNAc (OGT) protein; and (b) administering an effective amount of the nucleic acid or OGT protein to the myocyte or the heart, thereby increasing or normalizing SERCA2a expression, SERCA2a/PLB ratio and/or SERCA2a activity in the myocyte or the heart.

The invention provides methods for increasing or normalizing phosphorylation levels of PLB in a myocyte under hyperglycemic or diabetic conditions, or in a diabetic heart, the method comprising (a) providing a nucleic acid encoding an O-linked GlcNAc transferase (O-GlcNAc, OGT), wherein the nucleic acid is operatively linked to a promoter constitutively or inducibly active in the myocyte or the heart, or an O-GlcNAc (OGT) protein; and (b) administering an effective amount of the nucleic acid or OGT protein to the myocyte or the heart, thereby increasing or normalizing SERCA2a expression, SERCA2a/PLB ratio and/or SERCA2a activity in the myocyte or the heart.

The invention provides methods for increasing or normalizing SERCA2a promoter activity in a myocyte under hyperglycemic or diabetic conditions, or in a diabetic heart, the method comprising (a) providing a nucleic acid encoding an O-linked GlcNAc transferase (O-GlcNAc, OGT), wherein the nucleic acid is operatively linked to a promoter constitutively or inducibly active in the myocyte or the heart, or an O-GlcNAc (OGT) protein; and (b) administering an effective amount of the nucleic acid or OGT protein to the myocyte or the heart, thereby increasing or normalizing SERCA2a promoter activity in the myocyte or the heart.

The invention provides methods for reducing cellular O-GlcNAcylation in a myocyte under hyperglycemic or diabetic conditions, or in a diabetic heart, the method comprising (a) providing a nucleic acid encoding an O-linked GlcNAc transferase (O-GlcNAc, OGT), wherein the nucleic acid is operatively linked to a promoter constitutively or inducibly active in the myocyte or the heart, or an O-GlcNAc (OGT) protein; and (b) administering an effective amount of the nucleic acid or OGT protein to the myocyte or the heart, thereby reducing cellular O-GlcNAcylation in the myocyte or the heart.

The invention provides methods for reducing transcription factor Sp1 O-GlcNAcylation and increasing Sp1 activity in a myocyte under hyperglycemic or diabetic conditions, or in a diabetic heart, the method comprising (a) providing a nucleic acid encoding an O-linked GlcNAc transferase (O-GlcNAc, OGT), wherein the nucleic acid is operatively linked to a promoter constitutively or inducibly active in the myocyte or the heart, or an O-GlcNAc (OGT) protein; and (b) administering an effective amount of the nucleic acid or OGT protein to the myocyte or the heart, thereby reducing transcription factor Sp1 O-GlcNAcylation and increasing Sp1 activity in the myocyte or the heart.

The invention provides methods for normalizing myocyte-specific enhancer factor-2 (MEF-2a) levels in a myocyte under hyperglycemic or diabetic conditions, or in a diabetic heart, the method comprising (a) providing a nucleic acid encoding an O-linked GlcNAc transferase (O-GlcNAc, OGT), wherein the nucleic acid is operatively linked to a promoter constitutively or inducibly active in the myocyte or the heart, or an O-GlcNAc (OGT) protein; and (b) administering an effective amount of the nucleic acid or OGT protein to the myocyte or the heart, thereby normalizing the MEF-2a levels in the myocyte or the heart.

The invention provides methods for improving or normalizing cardiomyocyte contractility in a diabetic heart, the method comprising (a) providing a nucleic acid encoding an O-linked GlcNAc transferase (O-GlcNAc, OGT), wherein the nucleic acid is operatively linked to a promoter constitutively or inducibly active in a myocyte or the heart, or an O-GlcNAc (OGT) protein; and (b) administering an effective amount of the nucleic acid or OGT protein to the myocyte or the heart, thereby improving or normalizing cardiomyocyte contractility in the heart.

The invention provides methods for improving or normalizing global contractility in a diabetic heart, the method comprising (a) providing a nucleic acid encoding an O-linked GlcNAc transferase (O-GlcNAc, OGT), wherein the nucleic acid is operatively linked to a promoter constitutively or inducibly active in a myocyte or the heart, or an O-GlcNAc (OGT) protein; and (b) administering an effective amount of the nucleic acid or OGT protein to the myocyte or the heart, thereby improving or normalizing global contractility in the heart.

In an aspect of any method of the invention, the diabetes is type I diabetes or type II diabetes, or the hyperglycemic or diabetic conditions is caused by type I diabetes or type II diabetes, e.g., in humans. The hyperglycemic conditions can be caused by any condition, disease or metabolic state, e.g., a transient condition, such as diet, fasting, exercise and the like.

In an aspect of any method of the invention, administering the effective amount of the nucleic acid or OGT protein causes a reduction of abnormal, or excessive, O-GlcNAcylation in a cell, e.g., in a cytosolic and/or nuclear compartments, e.g., administration causes reduction in abnormal, or excessive, O-GlcNAcylation in a proteins in the cytosol and/or the nucleus of a cell.

The invention provides methods for improving myocardial performance (contractility) or global heart contractility in a mammal comprising a step of enhancing or increasing O-linked GlcNAc transferase (O-GlcNAc, OGT) transferase (O-GlcNAcase, O-GlcNAc, OGT) activity, the method comprising (a) providing (i) a nucleic acid encoding an O-linked GlcNAc transferase (O-GlcNAc, OGT), wherein the nucleic acid is operatively linked to a promoter constitutively or inducibly active in a myocyte or the heart, (ii) an O-GlcNAc (OGT) protein, (iii) a compound that relieves inhibition of O-GlcNAc (OGT) activity; or (iv) a compound that increases O-GlcNAc (OGT) transcription; and (b) administering an effective amount of the nucleic acid, protein or compound of (a) to the heart, thereby improving myocardial performance or global heart contractility in the heart.

In an aspect of any method of the invention, the cell is derived from a diabetic mammal, or the mammal is diabetic, e.g., the mammal is a diabetic human. In one aspect, the mammal is a mouse, a rat, a rabbit, a hamster, a dog, a pig, a sheep or a monkey.

The invention provides methods for improving myocardial performance (contractility) or global heart contractility in a diabetic mammal or a hyperglycemic mammal comprising (a) providing a pharmaceutical composition comprising (i) a nucleic acid encoding an O-linked GlcNAc transferase (O-GlcNAc, OGT), wherein the nucleic acid is operatively linked to a promoter constitutively or inducibly active in a myocyte or the heart, (ii) an O-GlcNAc (OGT) protein, (iii) a compound that relieves inhibition of O-GlcNAc (OGT) activity; or (iv) a compound that increases O-GlcNAc (OGT) transcription; and (b) administering an effective amount of the pharmaceutical composition to a subject in need thereof, thereby improving the myocardial performance (contractility) or global heart contractility in the diabetic mammal or hyperglycemic mammal.

The invention provides methods for treating, ameliorating or preventing heart disease comprising poor myocardial performance associated with diabetic cardiomyopathy, comprising (a) providing a pharmaceutical composition comprising (i) a nucleic acid encoding an O-linked GlcNAc transferase (O-GlcNAc, OGT), wherein the nucleic acid is operatively linked to a promoter constitutively or inducibly active in a myocyte or the heart, (ii) an O-GlcNAc (OGT) protein, (iii) a compound that relieves inhibition of O-GlcNAc (OGT) activity; or (iv) a compound that increases O-GlcNAc (OGT) transcription; and (b) administering an effective amount of the pharmaceutical composition to a subject in need thereof, thereby treating, ameliorating or preventing heart disease comprising poor myocardial performance associated with diabetic cardiomyopathy.

In alternative aspects, the subject having the diabetes, hyperglycemia, heart disease or cardiomyopathy is a diabetic mammal, and optionally the mammal is a human, a mouse, a rat, a rabbit, a hamster, a dog, a pig, a sheep or a monkey.

In an aspect of any method of the invention, the compound that increases O-GlcNAc (OGT) transcription comprises a transcriptional regulatory nucleic acid, and the method comprises inserting the transcriptional regulatory nucleic acid into the genome of a cell such that it increases transcription of O-GlcNAc (OGT) endogenous to the cell or relieves transcriptional inhibition of O-GlcNAc (OGT) endogenous to the cell, and optionally the transcriptional regulatory nucleic acid comprises a promoter or an enhancer.

The invention provides ex vivo methods for treating, ameliorating or preventing heart disease comprising poor myocardial performance associated with diabetic cardiomyopathy comprising (a) providing a cardiomyocyte, cardiomyocyte precursor cell or cardio-myocyte stem cell that overexpresses O-linked GlcNAc transferase (O-GlcNAc, OGT) by (i) inserting into the myocyte a nucleic acid encoding an O-linked GlcNAc transferase (O-GlcNAc, OGT), wherein the nucleic acid is operatively linked to a promoter constitutively or inducibly active in a myocyte or the heart, (ii) inserting into the myocyte an O-GlcNAc (OGT) protein, (iii) inserting into the myocyte a compound that relieves inhibition of O-GlcNAc (OGT) activity; (iv) inserting into the myocyte a compound that increases O-GlcNAc (OGT) transcription; or (v) inserting into the myocyte a transcriptional regulatory nucleic acid that it increases transcription of O-GlcNAc (OGT) endogenous to the cell or relieves transcriptional inhibition of O-GlcNAc (OGT) endogenous to the cell; and (b) administering the cardiomyocyte, cardiomyocyte precursor cell or cardio-myocyte stem cell to the heart of a subject in need thereof, thereby treating, ameliorating or preventing heart disease comprising poor myocardial performance associated with diabetic cardiomyopathy.

In an aspect of any method of the invention, an O-linked GlcNAc transferase (O-GlcNAc, OGT) nucleic acid is contained within (e.g., cloned within, or comprises) a cloning vehicle, an expression cassette or vector. In one aspect, the cloning vehicle, expression cassette or vector comprises a viral vector, a plasmid, a phage, a phagemid, a cosmid, a fosmid, a bacteriophage or an artificial chromosome. The viral vector can comprises an adenovirus vector, a retroviral vector or an adeno-associated viral vector, wherein optionally the retroviral vector comprises a lentiviral vector.

The invention provides pharmaceutical compositions, e.g., pharmaceutical compositions formulated for treating, ameliorating or preventing heart disease, comprising poor myocardial performance associated with diabetic cardiomyopathy, comprising (i) a nucleic acid encoding an O-linked GlcNAc transferase (O-GlcNAc, OGT), wherein the nucleic acid is operatively linked to a promoter constitutively or inducibly active in a myocyte or the heart, (ii) an O-GlcNAc (OGT) protein, (iii) a compound that relieves inhibition of O-GlcNAc (OGT) activity; or (iv) a compound that increases O-GlcNAc (OGT) transcription. The invention provides isolated cardiomyocyte cells, cardiomyocyte precursor cells or cardio-myocyte stem cells comprising: a nucleic acid encoding an O-linked GlcNAc transferase (O-GlcNAc, OGT), wherein the nucleic acid is operatively linked to a promoter constitutively or inducibly active in a myocyte or the heart, (ii) an exogenous O-GlcNAc (OGT) protein, (iii) a compound that relieves inhibition of O-GlcNAc (OGT) activity; and/or (iv) a compound that increases O-GlcNAc (OGT) transcription. In one aspect, the cell and/or the O-linked GlcNAc transferase (O-GlcNAc, OGT) are derived from a human.

The invention provides non-human transgenic animals comprising a heterologous O-linked GlcNAc transferase (O-GlcNAc, OGT) coding sequence. In one aspect, the animal is a goat, a rabbit, a sheep, a pig, a dog, a cow, a cat, a rat or a mouse. The endogenous O-linked GlcNAc transferase (O-GlcNAc, OGT) gene of the non-human transgenic animal is completely or partially disabled ("knocked out"). The invention provides cells, cell lines, tissues and organs derived from a non-human transgenic animals of the invention. The invention provides inbred animals, e.g., mouse inbred lines, derived from a non-human transgenic animals of the invention. The mouse line can comprise a human an O-linked GlcNAc transferase (O-GlcNAc, OGT).

Also provided herein are kits including instructions for practicing/using the nucleic acid constructs and/or cells and/or methods of the invention.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 10A illustrates mRNA expression of OGT; FIG. 10B illustrates protein expression of OGT; FIG. 10C illustrates mRNA expression of mouse GCA (mGCA), as described in detail in Example 2, below.

FIG. 13A: Panel A: averaged $Ca^{2+}$ transient; (FIG. 13B: Panel B: comparison of diastolic indo-1 ratio (Rdia), systolic indo-1 ratio (Rsys); FIG. 13C: Panel C: averaged normalized $Ca^{2+}$ transient; FIG. 13D: Panel D: comparison of diastolic decay time (Tdecay), as described in detail in Example 2, below.

Like reference symbols in the various drawings indicate like elements.

DETAILED DESCRIPTION

Figure 1A:
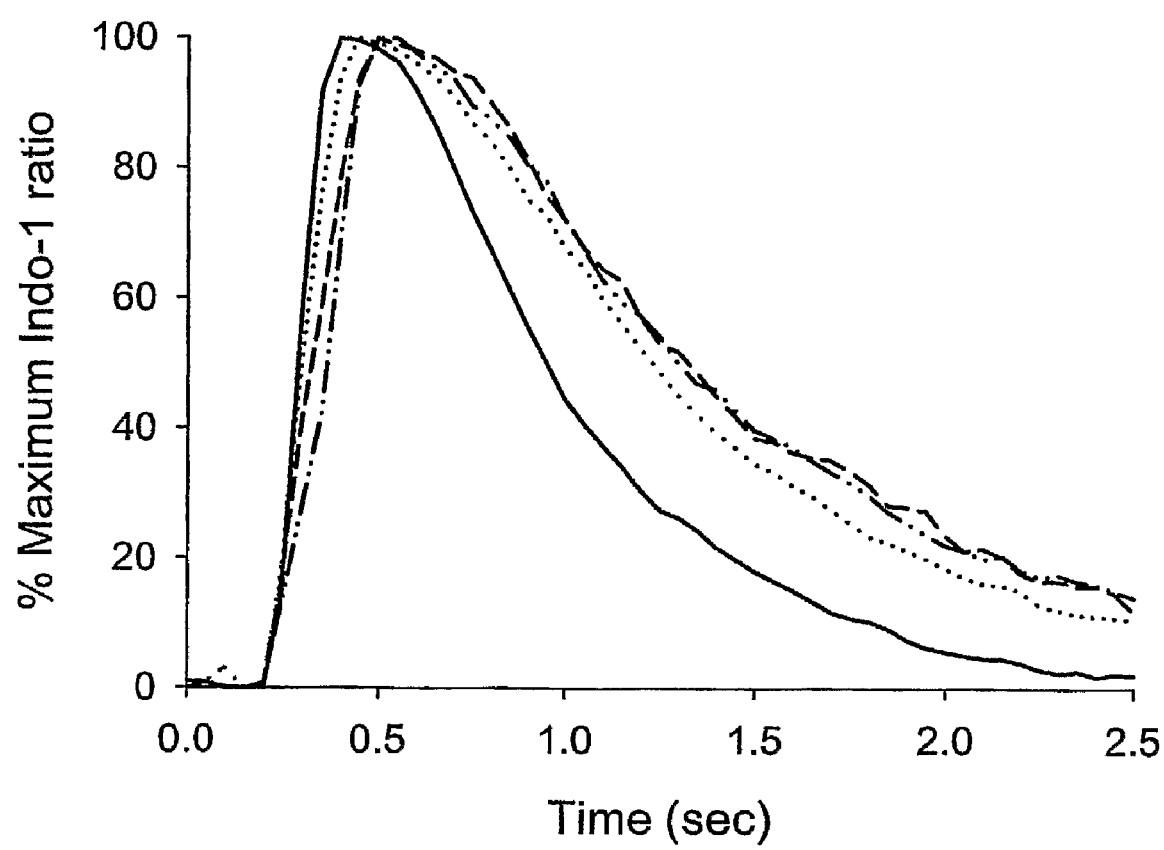
FIGS. 1A, 1B, 1C and 1D illustrate calcium transients measured in neonatal cardiomyocytes that were, inter alia, exposed to high glucose and infected with either adenovirus encoding O-GlcNAc transferase or O-GlcNAcase, as described in detail in Example 1, below.

The invention provides and describes the use of compositions, e.g., vectors, transduced or otherwise genetically engineered cells, and methods to express O-GlnNAcase ("OGT"), including human recombinant OGT, in vivo, ex vivo or in vitro, e.g., in alternative aspects, for gene therapy or for investigatory or drug screening use. In one aspect, the compositions and methods of the invention are used to treat, prevent or ameliorate heart disease associated with poor myocardial performance, e.g., diabetic cardiomyopathy and associated disorders.

The invention provides ex vivo and in vivo gene therapy for treating, preventing or ameliorating heart disease associated with poor myocardial performance, e.g., diabetic cardiomyopathy and associated disorders. In one aspect, the invention provides novel pharmaceutical formulations, as described herein. In one aspect, the invention provides O-GlnNAcase (OGT)-expressing "expression cassettes", or promoters operably linked to an O-GlnNAcase (OGT) coding sequence, e.g., the human OGT gene or equivalent enzyme expressing nucleic acid. In one aspect, the invention provides gene therapy reagents comprising recombinant viruses, e.g., adenoviruses or lentiviruses, that encode the full length of normal human O-GlnNAcase (OGT) (e.g., cDNA or genomic sequences) and various promoters that direct the expression of the enzyme. In one aspect, a promoter and/or other transcriptional regulatory elements (e.g., enhancers) directing expression of the O-GlnNAcase (OGT) is active in myocytes, cardiomyocytes and/or stem cells or cardiac stem cells in a constitutive and/or inducible manner.

The reagents of the invention can be used to prevent or ameliorate heart disease associated with poor myocardial performance, including diabetic cardio-myopathy and associated disorders, by, e.g., ex vivo and/or in vivo gene therapy. In one aspect, the invention provides a cloning or expression vehicle, e.g., a virus such as an engineered adenovirus or lentivirus, that expresses a full-length O-GlnNAcase (OGT) (e.g., the human OGT) in vitro, ex vivo and/or in vivo.

In one aspect, the invention provides a recombinant lentiviral vector to allow the viral infection of mammalian, e.g., human, tissues, including myocytes, cardiomyocytes and/or stem cells or cardiac stem cells. In addition, the nucleic acid constructs of the invention (e.g., recombinant viruses) can infect and integrate the transgene permanently into both dividing and non-dividing cells to mediate (generate) protein, e.g., O-GlnNAcase (OGT), expression. In alternative aspects, one or more wild type isozymes of the human O-GlnNAcase (OGT), or, sequence or structural modifications such as truncations or chimerics of human O-GlnNAcase (OGT), are used to practice the invention, e.g., in ex vivo and/or in vivo human gene therapy.

In one aspect, heart disease associated with poor myocardial performance, including diabetic cardio-myopathy and associated disorders, is treated, prevented or ameliorated by the compositions and methods of the invention by supplying disease-afflicted tissues or pre-diseased tissues (e.g., when the O-GlnNAcase (OGT) encoding sequence or protein is administered in predisposed individuals) with nucleic acids and/or O-GlnNAcase (OGT)-comprising formulations. The O-GlnNAcase (OGT) encoding nucleic acid constructs and/or O-GlnNAcase (OGT)-comprising formulations of the invention (e.g., viruses) can be directly or indirectly delivered to the heart, e.g., by direct injection of cells engineered to express O-GlnNAcase (OGT)-expressing nucleic acid or the O-GlnNAcase (OGT) enzyme itself, into the heart. In one aspect, when the O-GlnNAcase (OGT)-expressing nucleic acid or the O-GlnNAcase (OGT) enzyme is delivered sufficiently early, vector-mediated (e.g., viral mediated) expression of the wild type gene product will prevent and/or correct the heart disease associated with poor myocardial performance, including diabetic cardio-myopathy and associated disorders.

Described herein is a study demonstrating that the compositions and methods of the invention are effective for treating or ameliorating (or preventing) conditions and diseases associated with impaired cardiac contractility, such as that found associated with cardiomyopathies such as diabetic cardiomyopathy. The work described herein specifically investigated whether the impaired myocardial calcium cycling observed in diabetic cardiomyopathy is linked to O-GlcNAcylation in a hyperglycemia-dependent manner. Using cultured neonatal rat cardiomyocytes, we demonstrated that elevated extracellular glucose impairs calcium cycling, that these changes appear specifically via increased cellular O-GlcNAcylation, and that the detrimental effect of increased cellular O-GlcNAcylation can be mitigated against through administration O-GlcNAcase, e.g., in the example, by the use of adenovirally-transfected O-GlcNAcase protein, or in general by using the compositions and practicing the methods of the invention. Thus, the data presented herein demonstrates that the compositions and methods of the invention are effective for treating or ameliorating (or preventing) cardiomyopathies such as diabetic cardiomyopathy.

Diabetic cardiomyopathy, which is one aspect is treated, ameliorated and/or prevented by practicing the invention, is characterized by impaired cardiac contractility leading to poor myocardial performance. As discussed in Example 1, below, we investigated and demonstrated what role that the hexosamine pathway, and especially altered nuclear O-GlcNAcylation, plays in the development of diabetic cardiomyopathy. Incubating neonatal rat cardiomyocytes in high glucose (25 mM) resulted in prolonged calcium transients when compared with myocytes incubated in normal glucose (5.5 mM), which is consistent with delayed myocardial relaxation. High glucose-treated myocytes also exhibited reduced sarcoendoplasmic reticulum Ca-ATPase 2a (SERCA2a) mRNA and protein expression, decreased SERCA2a promoter activity, and increased O-GlcNAcylation of nuclear proteins compared with myocytes treated with normal glucose. Exposure of myocytes to 8 mM glucosamine or an adenovirus expressing O-GlcNAc transferase (OGT) resulted in prolonged calcium transient decays and significantly reduced SERCA2a protein levels, whereas treatment with an adenovirus encoding O-GlcNAcase (GCA) resulted in improved calcium transients and SERCA2a protein levels in myocytes exposed to high glucose. Effects of elevated glucose or altered O-GlcNAcylation were also observed on essential transcription factors involved in cardiomyocyte function. High glucose-treated myocytes (with or without OGT adenovirus) exhibited increased levels of O-GlcNAcylated Sp1 compared with control myocytes, whereas infecting high glucose-treated myocytes with GCA adenovirus reduced the degree of Sp1 GlcNAcylation. Treatment of myocytes with 25 mM glucose, 8 mM glucosamine, or OGT adenovirus also significantly reduced levels of myocyte-specific enhancer factor-2 (MEF-2A) protein compared with control myocytes, whereas infection with GCA adenovirus resulted in improved MEF2 expression. Our results demonstrated that the hexosamine pathway, and O-GlcNAcylation in particular, is important in impaired cardiac myocyte function and the development of diabetic cardiomyopathy.

As discussed in Example 2, below, to demonstrate that excessive protein O-GlcNAcylation plays a role in the dysfunction of the diabetic heart, we delivered adenovirus expressing O-GlcNAcase (Adv-GCA) into the myocardium of STZ-induced diabetic mice. Our results indicated that excessive cellular O-GlcNAcylation exists in the diabetic heart, and that in vivo GCA overexpression reduces overall cellular O-GlcNAcylation. Myocytes isolated from diabetic hearts receiving Adv-GCA exhibited improved calcium transients with a significantly shortened $T_{decay}$ (P<0.01) and increased sarcoplasmic reticulum $Ca^{2+}$ load (P<0.01). These myocytes also demonstrated improved contractility including a significant increase in +dL/dt and −dL/dt and greater fractional shortening as measured by edge detection (P<0.01). In isolated perfused hearts, developed pressure and −dP/dt were significantly improved in diabetic hearts receiving Adv-GCA (P<0.05). These hearts also exhibited a 40% increase in SERCA2a expression. Phospholamban protein expression was reduced 50%, but the phosphorylated form was increased 2 folds in the diabetic hearts receiving Adv-GCA. We conclude that excess O-GlcNAcylation in the diabetic heart contributes to cardiac dysfunction, and reducing this excess cellular O-GlcNAcylation has beneficial effects on calcium handling and diabetic cardiac function.

Generating and Manipulating Nucleic Acids

The invention provides isolated, recombinant and synthetic nucleic acids encoding an O-linked GlcNAc transferase (O-GlcNAc, OGT), e.g., a human O-linked GlcNAc transferase (O-GlcNAc, OGT) transferase for use in the compositions and methods of the invention, e.g., for insertion in a cardiomyocyte.

In one aspect, the term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include non-expressed DNA segments that, for example, form recognition sequences for other proteins. "Genes" can be obtained from a variety of sources, including cloning from a source of interest or synthesizing from known or predicted sequence information, and may include sequences designed to have desired parameters. The term "gene" includes a nucleic acid sequence comprising a segment of DNA involved in producing a transcription product (e.g., a message), which in turn is translated to produce a polypeptide chain, or regulates gene transcription, reproduction or stability. Genes can include regions preceding and following the coding region, such as leader and trailer, promoters and enhancers, as well as, where applicable, intervening sequences (introns) between individual coding segments (exons).

In one aspect, the term "genome" refers to the complete genetic material of an organism. In one aspect, the term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells, and organisms comprising transgenic cells are referred to as "transgenic organisms". The terms "transformed", "transduced", "transgenic", and "recombinant" refer to a host cell or organism into which a heterologous nucleic acid molecule has been introduced. The nucleic acid molecule can be stably integrated into the genome generally known in the art and are disclosed in Sambrook and Russell, infra. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

In one aspect, the terms "transfection of cells" refer to the acquisition by a cell of new nucleic acid material by incorporation of added DNA. Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-facilitated microparticle bombardment (Johnston (1990). Strontium phosphate DNA co-precipitation is also a transfection method.

In one aspect, the terms "transduction of cells" refer to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

"Operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

In one aspect, the term "promoter" includes all sequences capable of driving transcription of a coding sequence in a cell, e.g., a plant cell or animal cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

"Tissue-specific" promoters are transcriptional control elements that are only active in particular cells or tissues or organs, e.g., in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

The term "overexpression" refers to the level of expression in transgenic cells or organisms that exceeds levels of expression in normal or untransformed cells or organisms.

"Plasmids" can be commercially available, publicly available on an unrestricted basis, or can be constructed from available plasmids in accord with published procedures. Equivalent plasmids to those described herein are known in the art and will be apparent to the ordinarily skilled artisan.

In one aspect, the phrases "nucleic acid" or "nucleic acid sequence" includes oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin. The term encompasses nucleic acids, i.e., oligonucleotides, containing known analogues of natural nucleotides, naturally occurring nucleic acids, synthetic nucleic acids, and recombinant nucleic acids. The term also encompasses nucleic-acid-like structures with synthetic backbones, see e.g., Mata (1997) *Toxicol. Appl. Pharmacol.* 144:189-197; Strauss-Soukup (1997) *Biochemistry* 36:8692-8698; Samstag (1996) *Antisense Nucleic Acid Drug Dev* 6:153-156.

The skilled artisan will recognize that compounds used in the methods of the invention (e.g., catalytic, starting or intermediate compounds) can be synthesized using a variety of procedures and methodologies, which are well described in the scientific and patent literature, e.g., Organic Syntheses Collective Volumes, Gilman et al (Eds) John Wiley & Sons, Inc., NY; Venuti (1989) Pharm Res. 6:867-873. The invention can be practiced in conjunction with any method or protocol known in the art, which are well described in the scientific and patent literature.

In one aspect of the invention, a construct of the invention comprises a reporter or marker gene. The reporter or marker gene is used to monitor gene (e.g., O-linked GlcNAc transferase (O-GlcNAc, OGT)) expression. In particular, the reporter or marker gene is used to monitor gene suppression or silencing. In one aspect of the invention, the reporter gene is green fluorescent protein. Any compound, label, or gene that has a reporting or marking function can be used.

In another aspect, a constructs of the invention (e.g., a promoter of the invention operably linked to a heterologous sequence) are inserted into the genome of a host cell by e.g. a vector. A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

In alternative aspects, a vector used to make or practice the invention can be chosen from any number of suitable vectors known to those skilled in the art, including cosmids, YACs (Yeast Artificial Chromosomes), megaYACS, BACs (Bacterial Artificial Chromosomes), PACs (P1 Artificial Chromosome), MACs (Mammalian Artificial Chromosomes), a whole chromosome, or a small whole genome. The vector also can be in the form of or derived from a plasmid, a virus (e.g., an adenovirus, a lentivirus, and equivalent vectors) a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook. Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell. In one aspect of the invention, target sequences are integrated into genomes using a lentiviral feline immunodeficiency (FIV) vector for the transduction process.

The term "expression cassette" as used herein refers to a nucleotide sequence which is capable of affecting expression of a structural gene (i.e., a protein coding sequence, such as an enzyme of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers.

The term "expression cassette" as used herein refers to a nucleotide sequence which is capable of affecting expression of a nucleic acid or structural gene (e.g., an O-linked GlcNAc transferase (O-GlcNAc, OGT)-expressing nucleic acid) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers.

The invention provides non-human transgenic animals comprising a construct of the invention, e.g., a heterologous O-GlcNAc-expressing nucleic acid. In some aspects, the endogenous O-linked GlcNAc transferase (O-GlcNAc, OGT) gene of the non-human transgenic animal has been completely, or partially, disabled ("knocked out"). Nucleic acids used to practice the invention, including the human O-linked GlcNAc transferase (O-GlcNAc, OGT), and vectors comprising this or other nucleic acids can be made, isolated and/or manipulated by, e.g., cloning and expression of cDNA libraries, amplification of message or genomic DNA by PCR, and the like. In practicing the methods of the invention, homologous genes (e.g., encoding an O-linked GlcNAc transferase (O-GlcNAc, OGT)) can be modified by manipulating a template nucleic acid, as described herein. The invention can be practiced in conjunction with any method or protocol or device known in the art, which are well described in the scientific and patent literature.

The nucleic acids used to practice this invention, whether RNA, iRNA, siRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Alternatively, nucleic acids can be obtained from commercial sources.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., *Molecular Cloning: A Laboratory Manual* (2nd ed.), Vols. 1-3, Cold Spring Harbor Laboratory, (1989); *Current Protocols in Molecular Biology*, Ausubel, ed. John Wiley & Sons, Inc., New York (1997); *Laboratory Techniques in Biochemistry and Molecular Biology: Hybridization with Nucleic Acid Probes*, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In practicing the invention, nucleic acids of the invention or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., *PCR Protocols, A Guide to Methods and Applications*, ed. Innis, Academic Press, N.Y. (1990) and *PCR Strategies* (1995), ed. Innis, Academic Press, Inc., N.Y., ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) Proc. Natl. Acad. Sci. USA 86:1173); and, self-sustained sequence replication (see, e.g., Guatelli (1990) *Proc. Natl. Acad. Sci. USA* 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell. Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; and Sooknanan (1995) *Biotechnology* 13:563-564.

Transcriptional and Translational Control Sequences

The invention provides nucleic acid (e.g., O-linked GlcNAc transferase (O-GlcNAc, OGT)-expressing) sequences to practice the methods of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the *E. coli* lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used. Promoters suitable for expressing the polypeptide or fragment thereof in bacteria include the *E. coli* lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK) and the acid phosphatase promoter. Fungal promoters include the ∀ factor promoter. Eukaryotic promoters include the CMV immediate early promoter, the HSV thymidine kinase promoter, heat shock promoters, the early and late SV40 promoter, LTRs from retroviruses and the mouse metallothionein-I promoter. Other promoters known to control expression of genes in prokaryotic or eukaryotic cells or their viruses may also be used.

Cells and Tissues

The invention also provides cells and tissues (e.g., harvested from a transgenic animal of the invention) comprising a nucleic acid construct of the invention; in one aspect, comprising the human encoding an O-linked GlcNAc transferase (O-GlcNAc, OGT) gene or equivalent O-linked GlcNAc transferase (O-GlcNAc, OGT) transferase coding sequence. Animal cells comprising a nucleic acid construct of the invention include non-human and human mammalian cells. Exemplary animal cells of the invention include CHO, COS or Bowes melanoma or any mouse or human cell line. The selection of an appropriate host is within the abilities of those skilled in the art.

Where appropriate, host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction).

The invention also provides transformed cells comprising a nucleic acid for practicing the methods of the invention, e.g., an O-linked GlcNAc transferase (O-GlcNAc, OGT) gene or equivalent O-linked GlcNAc transferase (O-GlcNAc, OGT) transferase coding sequence. The host cell may be any of the host cells familiar to those skilled in the art, including prokaryotic cells, eukaryotic cells, such as bacterial cells, fungal cells, yeast cells, mammalian (e.g., mouse, human) cells, insect cells, or plant cells.

The vector can be introduced into the host cells using any of a variety of techniques, including transformation, transfection, transduction, viral infection, gene guns, and the like.

Exemplary methods include calcium phosphate transfection, DEAE-Dextran mediated transfection, lipofection, or electroporation.

In one aspect, the nucleic acids or vectors of the invention are introduced into the cells in a manner suitable for subsequent expression of the nucleic acid. The method of introduction is largely dictated by the targeted cell type. Exemplary methods include CaPO$_4$ precipitation, liposome fusion, lipofection (e.g., LIPOFECTIN™), electroporation, viral infection, etc. The candidate nucleic acids may stably integrate into the genome of the host cell (for example, with retroviral, e.g., lentiviral, based introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets can be used.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Transgenic Non-Human Animals

The invention provides transgenic non-human animals comprising a nucleic acid construct of the invention, including an expression cassette or vector or a transfected or transformed cell comprising a nucleic acid expressing an O-linked GlcNAc transferase (O-GlcNAc, OGT) transferase operably linked to promoter and/or enhancer. The invention also provides methods of making and using these transgenic non-human animals.

The transgenic non-human animals can be, e.g., goats, rabbits, sheep, pigs, cows, rats and mice, comprising a nucleic acid construct of the invention. These animals can be used, e.g., as in vivo models for O-linked GlcNAc transferase (O-GlcNAc, OGT) transferase, e.g., human O-linked GlcNAc transferase (O-GlcNAc, OGT) expression and activity, e.g., as models to screen for compound that can activate human O-linked GlcNAc transferase (O-GlcNAc, OGT) gene activity in vivo.

The coding sequences for the polypeptides to be expressed in the transgenic nonhuman animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express an endogenous gene, e.g., the endogenous O-linked GlcNAc transferase (O-GlcNAc, OGT) gene locus, or subsequences thereof. "Knockouts" can be prepared by deletion or disruption by homologous recombination of an endogenous promoter. Homologous recombination and other means to alter (and "knockout") expression of endogenous sequences is well known in the art and is described in, e.g., U.S. Pat. Nos. 5,464,764; 5,631,153; 5,487,992; 5,627,059, and 5,272,071.

Polypeptides and Peptides

In alternative aspects of the invention, the methods are practiced by administering O-linked GlcNAc transferase (O-GlcNAc, OGT) polypeptides, e.g., the exemplary SEQ ID NO:1, to a cell or to a subject, e.g., in the form of a pharmaceutical composition—particularly to target cardiomyocytes.

Polypeptides and peptides (e.g., containing O-linked GlcNAc transferase active sites) used to practice the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered from an exemplary polypeptide of the invention. In one aspect, a mimetic composition is used in a composition, cell system or process of the invention (e.g., a host cell having a plasmid expressing at least one enzyme of the invention).

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY). A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

Polypeptides used to practice the method of the invention (e.g., O-linked GlcNAc transferase (O-GlcNAc, OGT)) can be modified by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins-Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize O-linked GlcNAc transferase (O-GlcNAc, OGT). Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

O-linked GlcNAc Transferase (O-GlcNAc, OGT) Proteins Nucleic Acids Encoding them The invention provides O-linked GlcNAc transferase (O-GlcNAc, OGT) polypeptides and nucleic acid constructs, engineered cells and non-human transgenic animals, and methods of using them, comprising OGT sequences, including, for example Homo sapiens OGT-encoding sequence as set forth in, e.g., in GenBank accession nos. O15294, Q96CC1; secondary accession nos. Q7Z3K0 Q8WWM8 Q96CC1 Q9UG57; see EC 2.4.1.-. See also EMBL U77413; AAB63466.1; -; mRNA; AJ315767; CAC86127.1; -; Genomic_DNA; AJ315767; CAC86128.1; -; Genomic_DNA; AJ315767; CAC86129.1; -; Genomic_DNA; AL050366; CAB62528.1; ALT_INIT; mRNA; AL833085; CAD89970.1; -; mRNA; BX537844; CAD97853.1; -; mRNA; BC014434; AAH14434.1; -; mRNA; BC038180; AAH38180.1; -; mRNA.

Any isoform of OGT can be used in practicing the invention; e.g., see Lubas (1997) J. Biol. Chem. 272(14):9316-9324.

For example, an expression cassette of the invention can comprise, or, a promoter of the invention can be operably linked, to a nucleic acid encoding one or more or all of the following OGT sequences, or fragments thereof, including coding or non-coding sequences of:

```
MASSVGNVAD STEPTKRMLS FQGLAELAHR EYQAGDFEAA ERHCMQLWRQ EPDNTGVLLL    (SEQ ID NO: 1)

70         80         90        100        110        120
LSSIHFQCRR LDRSAHFSTL AIKQNPLLAE AYSNLGNVYK ERGQLQEAIE HYRHALRLKP
```

```
        130        140        150        160        170        180
DFIDGYINLA AALVAAGDME GAVQAYVSAL QYNPDLYCVR SDLGNLLKAL GRLEEAKACY 190        200        210        220        230        240
LKAIETQPNF AVAWSNLGCV FNAQGEIWLA IHHFEKAVTL DPNFLDAYIN LGNVLKEARI 250        260        270        280        290        300
FDRAVAAYLR ALSLSPNHAV VHGNLACVYY EQGLIDLAID TYRRAIELQP HFPDAYCNLA 310        320        330        340        350        360
NALKEKGSVA EAEDCYNTAL RLCPTHADSL NNLANIKREQ GNIEEAVRLY RKALEVFPEF 370        380        390        400        410        420
AAAHSNLASV LQQQGKLQEA LMHYKEAIRI SPTFADAYSN MGNTLKEMQD VQGALQCYTR 430        440        450        460        470        480
AIQINPAFAD AHSNLASIHK DSGNIPEAIA SYRTALKLKP DFPDAYCNLA HCLQIVCDWT 490        500        510        520        530        540
DYDERMKKLV SIVADQLEKN RLPSVHPHHS MLYPLSHGFR KAIAERHGNL CLDKINVLHK 550        560        570        580        590        600
PPYEHPKDLK LSDGRLRVGY VSSDFGNHPT SHLMQSIPGM HNPDKFEVFC YALSPDDGTN 610        620        630        640        650        660
FRVKVMAEAN HFIDLSQIPC NGKAADRIHQ DGIHILVNMN GYTKGARNEL FALRPAPIQA 670        680        690        700        710        720
MWLGYPGTSG ALFMDYIITD QETSPAEVAE QYSEKLAYMP HTFFIGDHAN MFPHLKKKAV 730        740        750        760        770        780
IDFKSNGHIY DNRIVLNGID LKAFLDSLPD VKIVKNKCPD GGDNADSSNT ALNMPVIPMN 790        800        810        820        830        840
TIAEAVIEMI NRGQIQITIN GFSISNGLAT TQINNKAATG EEVPRTIIVT TRSQYGLPED 850        860        870        880        890        900
AIVYCNFNQL YKIDPSTLQM WANILKRVPN SVLWLLRFPA VGEPNIQQYA QNMGLPQNRI 910        920        930        940        950        960
IFSPVAPKEE HVRRGQLADV CLDTPLCNGH TTGMDVLWAG TPMVTMPGET LASRVAASQL 970        980        990       1000       1010       1020
TCLGCLELIA KNRQEYEDIA VKLGTDLEYL KKVRGKVWKQ RISSPLFNTK QYTMELERLY 1030       1040
LQMWEHYAAG NKPDHMIKPV EVTESA
```

Kits and Libraries

The invention provides kits comprising compositions and methods of the invention, including cells comprising heterologous O-linked GlcNAc transferase (O-GlcNAc, OGT) coding sequences, O-linked GlcNAc transferase (O-GlcNAc, OGT)-expression vehicles, transfecting agents, transducing agents, instructions (regarding the methods of the invention), or any combination thereof. As such, kits, cells, vectors and the like are provided herein.

Pharmaceutical Compositions

The invention provides pharmaceutical compositions comprising an O-linked GlcNAc transferase (O-GlcNAc, OGT) or an O-linked GlcNAc transferase (O-GlcNAc, OGT)-expressing nucleic acid (e.g., a vector, virus, and the like) and a pharmaceutically acceptable excipient. The invention provides parenteral formulations comprising O-linked GlcNAc transferase (O-GlcNAc, OGT) protein or nucleic acids expressing O-linked GlcNAc transferase (O-GlcNAc, OGT). The invention provides enteral formulations comprising an O-linked GlcNAc transferase (O-GlcNAc, OGT) or an O-linked GlcNAc transferase (O-GlcNAc, OGT)-expressing nucleic acid. The invention provides methods for improving or normalizing cardiomyocyte contractility in a diabetic heart comprising providing a pharmaceutical composition comprising an O-linked GlcNAc transferase (O-GlcNAc, OGT) or an O-linked GlcNAc transferase (O-GlcNAc, OGT)-expressing nucleic acid; and administering an effective amount of the pharmaceutical composition to a subject in need thereof.

The invention provides, in addition to methods for methods for improving myocardial performance (contractility) or global heart contractility in a mammal, methods for decreasing the calcium transient ($T_{1/2}$) intracellular calcium flux in a myocyte under hyperglycemic or diabetic conditions, methods for ameliorating diastolic impairment in calcium flux in a diabetic heart, methods for improving (normalizing) calcium cycling in a myocyte under hyperglycemic or diabetic conditions, or a diabetic heart, by enhancing the $Ca^{2+}$ transient and sarcoplasmic reticulum $Ca^{2+}$ loading (see Summary for addition methods of the invention). These methods can be practiced in vivo, ex vivo or in vitro. In this aspect, the method comprises providing a pharmaceutical composition comprising an O-linked GlcNAc transferase (O-GlcNAc, OGT) or an O-linked GlcNAc transferase (O-GlcNAc, OGT)-expressing nucleic acid; and administering an effective amount of the pharmaceutical composition to a subject in need thereof.

The pharmaceutical compositions used in the methods of the invention can be administered by any means known in the art, e.g., parenterally, topically, orally, or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a chimeric polypeptide or peptidomimetic of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration of hydrophobic active agents of the invention. Oil-based suspensions can be formulated by suspending an active agent (e.g., a chimeric composition of the invention) in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In the methods of the invention, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In the methods of the invention, the pharmaceutical compounds can be delivered by transdermally, by a topical route, formulated as applicator sticks, solutions, suspensions, emulsions, gels, creams, ointments, pastes, jellies, paints, powders, and aerosols.

In the methods of the invention, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In the methods of the invention, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations of the invention can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations of the invention can be administered for prophylactic and/or therapeutic treatments, e.g., for improving or normalizing cardiomyocyte contractility in a diabetic heart. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). In the methods of the invention, a pharmaceutical composition is administered in an amount sufficient to treat (e.g., ameliorate) or prevent cardiomyopathy in a diabetic heart. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat the treat (e.g., ameliorate) or prevent cardiomyopathy in a diabetic heart, or, for improving myocardial performance (contractility) or global heart contractility in a mammal. For example, an exemplary pharmaceutical formulation for oral administration of O-linked GlcNAc transferase (O-GlcNAcase, O-GlcNAc, OGT) is in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The compositions and formulations of the invention can further comprise other drugs or pharmaceuticals, e.g., compositions for treating septic shock, infection, fever, pain and related symptoms or conditions. The methods of the invention can further comprise co-administration with other drugs or pharmaceuticals, e.g., compositions for treating septic shock, infection, fever, pain and related symptoms or conditions. For example, the methods and/or compositions and formulations of the invention can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

The invention provides means of in vivo delivery of nucleic acids encoding an O-linked GlcNAc transferase (O-GlcNAc, OGT); wherein in one aspect the nucleic acid is operatively linked to a promoter constitutively or inducibly active in a myocyte or a heart. In one aspect, the invention uses vector constructs that are targeted for delivery and/or expression in the myocardium. In another aspect, the invention uses vector constructs that are not otherwise targeted for delivery and/or expression that is restricted to the myocardium, e.g., by injection of the vector into a blood vessel directly supplying the myocardium, e.g., by injection into a coronary artery. Such injection can be achieved by catheter introduced substantially (typically at least about 1 cm) within the ostium of one or both coronary arteries or one or more saphenous veins or internal mammary artery grafts or other conduits delivering blood to the myocardium. By injecting a vector deeply into the lumen of one or both coronary arteries (or grafts and other vascular conduits), in one aspect, into both the right and left coronary arteries (or grafts and other vascular conduits), e.g., in an amount of $10^7$ to $10^{13}$ viral particles as determined by optical densitometry, it is possible to locally transfect a desired number of cells, especially cardiac myocytes, with genes that will express O-linked GlcNAc transferase (O-GlcNAc, OGT) in the affected myocardium, thereby maximizing therapeutic efficacy of gene transfer, and minimizing undesirable effects at extracardiac sites, e.g., the possibility of an inflammatory response to viral proteins.

Vector constructs that are specifically targeted to the myocardium, such as vectors incorporating myocardial-specific binding or uptake components, and/or which incorporate O-linked GlcNAc transferase (O-GlcNAc, OGT) transgenes that are under the control of myocardial-specific transcriptional regulatory sequences (e.g., ventricular myocyte-specific promoters) can be used in place of or, depending on the application, preferably, or in addition to, such directed injection techniques as a means of further restricting expression to the myocardium, especially the ventricular myocytes. For vectors that can elicit an immune response, it is preferable to inject the vector directly into a blood vessel supplying the myocardium as described above, although the additional techniques for restricting the potential for extracardiac expression can also be employed. See, e.g., U.S. Pat. No. 6,306,830.

The invention can also be practiced using techniques including penetrating catheters to deliver O-linked GlcNAc transferases and/or nucleic acids that encode them, or cells expressing them, such as those as described in U.S. Pat. No. 6,602,241, describing methods and apparatus for delivery of substances or apparatus to target sites located outside blood vessels within the body of a human or animal patient. A vessel wall penetrating catheter is inserted into the vasculature, positioned and oriented within a blood vessel near the target extravascular site and a penetrator is advanced from the catheter so as to penetrate outwardly through the wall of the blood vessel in the direction of the target site. Alternatively, a delivery catheter having an occlusion member or balloon may be advanced into a vein or venule and the occlusion member or balloon may be used to occlude the lumen of the vein or venule during and after injection of a substance through the catheter, such that the substance will not be carried away by normal venous blood flow and will remain in the vein or venule for a sufficient period of time to have its intended effect (e.g. to enter adjacent tissues through capillary beds drained by that vein or venule).

The invention can also be practiced using techniques for direct in vivo electrotransfection, e.g., as described in U.S. Pat. No. 6,519,492, describing method for direct in vivo electrotransfection of a plurality of cells of a target tissue where the target is perfused with a transfection solution. An exterior electrode is positioned so as to surround at least a portion of the target tissue. One or more interior electrodes are placed within the target tissue. The perfusion and the application of the interior and exterior electrodes may be performed in any particular order. After the perfusion and the positioning of the electrodes, both interior and exterior, an electric waveform is applied through the exterior electrode and the interior electrode to transfect the cells in the target tissue.

The invention will be further described with reference to the following examples; however, it is to be understood that the invention is not limited to such examples.

EXAMPLES

Example 1

Diabetes and the Accompanying Hyperglycemia Impairs Cardiomyocyte Calcium Cycling Through Increased Nuclear O-GlcNAcylation The following example describes making and using exemplary compositions and methods of the invention. This example describes a study demonstrating that the compositions and methods of the invention are effective for treating or ameliorating (or preventing) conditions and diseases associated with impaired cardiac contractility, such as that found associated with cardiomyopathies such as diabetic cardiomyopathy. The data presented herein demonstrate, inter alia, that the compositions and methods of the invention are effective for treating or ameliorating (or preventing) cardiomyopathies such as diabetic cardiomyopathy.

Specifically investigated was whether the impaired myocardial calcium cycling observed in diabetic cardiomyopathy is linked to O-GlcNAcylation in a hyperglycemia-dependent manner. Using cultured neonatal rat cardiomyocytes, we demonstrated that elevated extracellular glucose impairs calcium cycling, that these changes appear specifically via increased cellular O-GlcNAcylation, and that the detrimental effect of increased cellular O-GlcNAcylation can be mitigated against through administration O-GlcNAcase, e.g., in the example, by the use of adenovirally-transfected O-GlcNAcase protein, or in general by using the compositions and practicing the methods of the invention.

Experimental Methods

Materials Antibodies used in this study were: anti-Sp1 (07-124, Upstate Biotechnology, Lake Placid, N.Y.), anti-MEF-2 (predominantly MEF-2a, sc-313, Santa Cruz Biotechnology, Santa Cruz, Calif.), anti-O-GlcNAc monoclonal (CTD 110.6, provided as a gift by Dr. Gerald Hart, Johns Hopkins University, Baltimore, Md.; see Comer (2001) Anal. Biochem. 293:169-177), and horseradish peroxidase-conjugated anti-rabbit IgG (Amersham Biosciences) and anti-mouse IgM (Sigma). Indo-1/AM and Pluronic were purchased from Molecular Probes (Eugene, Oreg.). Pre-cast Tris/Glycine SDS gels and all electrophoresis supplies were from Bio-Rad (Hercules, Calif.). PUGNAc, or O-(2-acetamido-2-deoxy-D-glucopyranosylidene)amino-N-phenyl carbamate, was purchased from Toronto Research Chemicals (North York, Ontario, Canada). All other chemicals were purchased from Sigma unless otherwise noted.

Cardiomyocyte Isolation and Culture. Primary cultures of neonatal rat cardiomyocytes were prepared as described previously, see, e.g., Hartong (1996) J. Mol. Cell. Cardiol. 28:2467-2477. Cells were plated onto gelatin-coated culture dishes or laminin-coated glass chamber slides. Plating medium consisted of 4.25:1 DMEM:M199, 10% horse serum, 5% fetal bovine serum, 1% penicillin/streptomycin/fungizone (PSF), and 5.5 mM D-glucose. Cells were allowed to adhere to the plates for 24 hours before changing to basic experimental culture medium (4.5:1 DMEM:M199, 2% fetal bovine serum, 1% PSF, and 100 μM insulin) and supplemented with glucose at either physiological (5.5 mM; normal glucose) or elevated (25 mM; high glucose) concentrations. For some experiments, media was supplemented with 8 mM glucosamine, 40 μM aminoguanidine, 0.5 μg/ml tunicamycin, 50 μM PUGNAc or an osmotic control (20 mM mannitol). In cases where cells were plated at exceptionally high density ($5 \times 10^6$ per 100 mm plate), the culture medium was changed daily until the cells were harvested.

Construction of adenoviral vectors. The rat cDNA corresponding to the UDP-N-acetylglucosamine:peptide N-acetylglucosaminyl transferase gene (O-GlcNAc transferase; OGT), which encodes the enzyme responsible for the O-linkage of single N-acetylglucosamine molecules to serine/threonine residues (19), and the human cDNA encoding the O-GlcNAcase gene (GCA), the enzyme responsible for removing O-linked N-acetylglucosamine residues (see, e.g., Haltiwanger (1992) J. Biol. Chem. 267:9005-9013). Each cDNA was inserted into the E1 region of an adenoviral vector construct using previously described methods (see, e.g., Gao (2001) J. Biol. Chem. 276:9838-9845). Replication-deficient adenovirus particles containing the target gene or empty vector (SR−) were generated by in vivo recombination in 293 cells and single plaques were isolated and propagated to achieve high titer. Adenoviral particles were CsCl-purified and quantified by plaque titer assay. Myocytes were infected with a multiplicity of infection (MOI) of 25 for all viruses.

Measurement of $[Ca^{2+}]_i$ transients. Indo-1 facilitated measurement of $Ca^{2+}$ transients has been described previously, see, e.g., He (1997) J. Clin. Invest 100:380-389). Briefly, cells were plated ($5 \times 10^4$) onto glass chamber slides and incubated for 48-72 hours in experimental medium as above. Cells were rinsed twice with appropriate serum-free culture medium (5.5 or 25 mM glucose) then incubated with the same medium containing 10 μM Indo-1/AM, 1 mg/ml bovine serum albumin, and 0.01% (wt/vol) PLURONIC F-127™ for 30 minutes in a 37° C. incubator. Cells were rinsed and incubated for 20 min at RT in appropriate serum-free culture medium containing 1.8 mM $CaCl_2$ prior to making fluorescence measurements to allow for deesterification of the Indo-1/AM. Myocytes were stimulated to contract (0.3 HZ) using platinum electrodes, and Indo-1 ratios (405/484 nm) were collected at 20 Hz at room temperature using methods and equipment as described previously, see, e.g., McDonough (1994) J. Biol. Chem. 269:9466-9472). Diastolic and systolic $Ca^{2+}$ levels were defined as the resting ratio and maximal ratio per cycle, respectively. Transients were measured from at least 18 cells per slide per treatment. For data analysis, transients were aligned and averaged using the initial upstroke of each transient as a reference point, then normalized using the diastolic and systolic ratios as references.

Western Immunoblotting. To determine SERCA2a protein levels, myocytes ($1 \times 10^6$) were washed with phosphate buffered saline (PBS), then extracted with 0.2 ml lysis buffer (20 mM Tris, pH 7.4, 20 mM NaCl, 0.1 mM EDTA, 1% Triton X-100, 0.5% Na-deoxycholate, 1 mM dithiothreitol). Lysates were incubated on ice for 30 min, and cellular debris was pelleted at 10,000×g for 20 min at 4° C. Protein concentration in the supernatant was determined by BioRad protein reagent. 30 μg of protein diluted in extraction buffer and 4× Laemmli sample buffer were loaded without boiling onto pre-cast 4-20% Tris-glycine gels. Separated proteins were transferred to nylon membranes using a Bio-Rad Mini Trans-Blot apparatus and blocked overnight at 4° C. Blots were incubated with a rabbit polyclonal SERCA2a antibody (see, e.g., Hartong (1996) supra) (1:5000) for 1 hour at RT, followed by a 1 hour incubation with a 1:5000 dilution of goat anti-rabbit IgG-HRP conjugated secondary antibody (Amersham). Bands were visualized by reacting with chemiluminescent substrate (NEN) and exposed to film. Protein bands were quantified from scanned images using Scion imaging software (Scion, Frederick, Md.).

To examine cellular O-GlcNAcylation and MEF-2a levels, nuclear extracts were prepared from neonatal cardiomyocytes ($2 \times 10^6$) using modifications of the procedures described by Dignam (1983) Nucleic Acids Res. 11:1475-1489. Samples of each extract (25-50 μg) were fractionated by SDS-PAGE on precast 4-20% Tris-glycine gels (BioRad) and transferred to nylon membranes. Membranes were blocked overnight, exposed to the O-GlcNAc-specific antibody 110.6 (17) (1:10,000) overnight at 4° C., then exposed for 1 hour to 1:5,000 goat anti-mouse IgM-HRP. Alternatively, membranes were exposed to anti-MEF-2 (1:200) for one hour at RT followed by a one hour exposure to 1:10,000 goat anti-rabbit IgG-HRP. Visualization and quantification was as described above.

Sp1 Immunoprecipitation. Nuclear extracts were made from neonatal cardiomyocytes ($5 \times 10^6$) using the procedures of Dignam (1983) supra. Protein (50 μg) was diluted to 0.5 ml with binding buffer (10 mM Tris pH 7.9, 2 mM $MgCl_2$, 0.15 mM NaCl, 1 mM dithiothreitol, 10% glycerol, and 1 mM PMSF) and incubated with 4 μg of anti-Sp1 antibody (Santa Cruz Biotech) on a rotator for two hours at 4° C., followed by overnight incubation with 20 μl of protein A/G plus agarose (Santa Cruz Biotech.). Immunoprecipitates were washed four times in RIPA buffer, resuspended in 40 μl of 1× sample buffer and boiled for 3 minutes, separated on 7.5% Tris-glycine gels and transferred to nylon membranes. Blots were incubated for 1 hour with the same antibody used to IP Sp1 (1:1000 in TBSTM) followed by exposure to a goat anti-rabbit IgG-HRP secondary antibody (1:20,000 in TBSTM). Visualization and quantification were as described above.

Northern Blot Analysis. Cellular RNA was extracted from cultured myocytes using the guanidine thiocyanate method (Chomczynski (1987) Anal. Biochem. 162:156-159) as described previously, e.g., by Trost (2002) Diabetes 51:1166-1171. The RNA was fractionated on a 1% agarose gel and transferred to a nylon membrane. A 1.6 kb fragment of the 5' end of a cDNA of the rat SERCA2a gene was used to generate a $^{32}$P-labeled probe (MULTIPRIME™ DNA labeling system, Amersham). A probe for 28S rRNA was used as a loading control. Bands were visualized on radiographic film and the resulting images scanned and quantified using SCION™ imaging software.

Transfections and SERCA2a Promoter Luciferase Assays. DNA transfection of neonatal cardiomyocytes was performed using the calcium phosphate-DNA co-precipitation method, see, e.g., Chen (1987) Mol. Cell. Biol 7:2745-2752. Cells ($0.5 \times 10^6$) were transfected overnight in appropriate culture medium (either NG- or HG-containing medium) with 50 ng of either a 0.6 kb fragment of the rat SERCA2a promoter (corresponding to the 600 bases immediately upstream of the transcriptional start codon) (see, e.g., Rohrer (1991) J. Biol. Chem. 266:8638-8646) or a control plasmid (pGL3; Promega) and 3 μg of fill plasmid (pBS; Stratagene), then washed with PBS and changed into fresh culture medium. Cells to be treated with adeno-OGT or adeno-GCA were first infected with an MOI of 25 followed 24 hours later by transfection. Transfected cells were incubated for 48 hours, then washed with PBS and incubated for 10 min with gentle agitation at RT in 200 μl of harvest buffer (50 mM MES/Tris pH 7.8, 0.1% Triton X-100, and 1.3 mM dithiothreitol).

Luciferase activity was measured using 100 μl of extract in a luminometer.

Animals and Determination of Cardiac Sugar Nucleotides. Male CB6F1 mice weighing 20-25 g (Charles River, Wilmington, Mass.) were made diabetic using methods described previously, see, e.g., Trost (2002) supra. Briefly, diabetes was induced with a single intraperitoneal injection of streptozocin (150 mg/kg in citrate saline, pH 4.5) to animals fasted overnight (16 hrs). Diabetic animals were sacrificed three weeks following injection. To determine the degree of diabetes, blood was drawn via direct cardiac puncture in $CO_2$-euthanized animals and plasma glucose concentration was determined using the Sigma Glucose Kit (510-A).

Sugar nucleotides were extracted from fresh ventricles and quantified by HPLC as described by Weckbecker (1983) Anal. Biochem. 132:405-412. Hearts were homogenized in 3 vols of ice-cold 0.3 M $HClO_4$ and debris pelleted at 10,000×g for 15 min at 4° C. Two vols of 1:4 trioctylamine: 1,1,2-trichlorotrifluoroethane (Freon) were added to the supernatant, followed by vortexing for 30 sec and centrifuging at 1000×g for 5 min at 4° C. The aqueous phase was carefully transferred to a fresh tube and frozen at −80° C. until assayed. Samples were diluted in 0.5 ml $H_2O$ and desalted on a Mono-Q column (flow rate 1 ml/min). The combined UDP-GlcNAc/GalNAc fraction was collected as a peak at 23 minutes and the sample was lyophilized overnight. Dried samples were subsequently dissolved in borate solution (0.22 M boric acid, 0.09 M disodium tetraborate, and 1.2 M glycerol, pH 6.85), and separated into distinct UDP-GlcNAc and UDP-GalNAc peaks on a Partisil SAX-10 column. Calibration of the peaks was performed by processing known amounts of UDP-GlcNAc and UDP-GalNAc using the same methods as above and comparing total area under the curve for the experimental vs. control peaks for each fraction.

Data Collection and Statistical Analysis. Experimental treatments were evaluated on myocyte cultures from at least three different isolations to control for variation among cultures. Data are presented as mean±SEM. Statistical significance (P<0.05) was evaluated using one-way ANalysis Of VAriance between groups (ANOVA) (SigmaStat, Chicago, Ill.). Post-hoc multiple comparisons for calcium transients were made using a Student-Newman-Keuls test.

Results

Calcium transients. To determine whether elevated extracellular glucose and increased O-GlcNAcylation would exert an effect on intracellular calcium flux, Indo-1 calcium transients were determined in neonatal rat cardiomyocytes. Because the exact $Ca^{2+}$-binding dynamics of Indo-1 are uncertain, and given that Indo-1 has the potential to be compartmentalized intracellularly, we present data as the ratio of Indo-1 fluorescence observed at 405 and 485 nm, rather than as a calculated intracellular calcium concentration. To simplify comparisons, we also normalized transients to the diastolic (basal) and systolic (maximal) ratios.

Figure 1B:
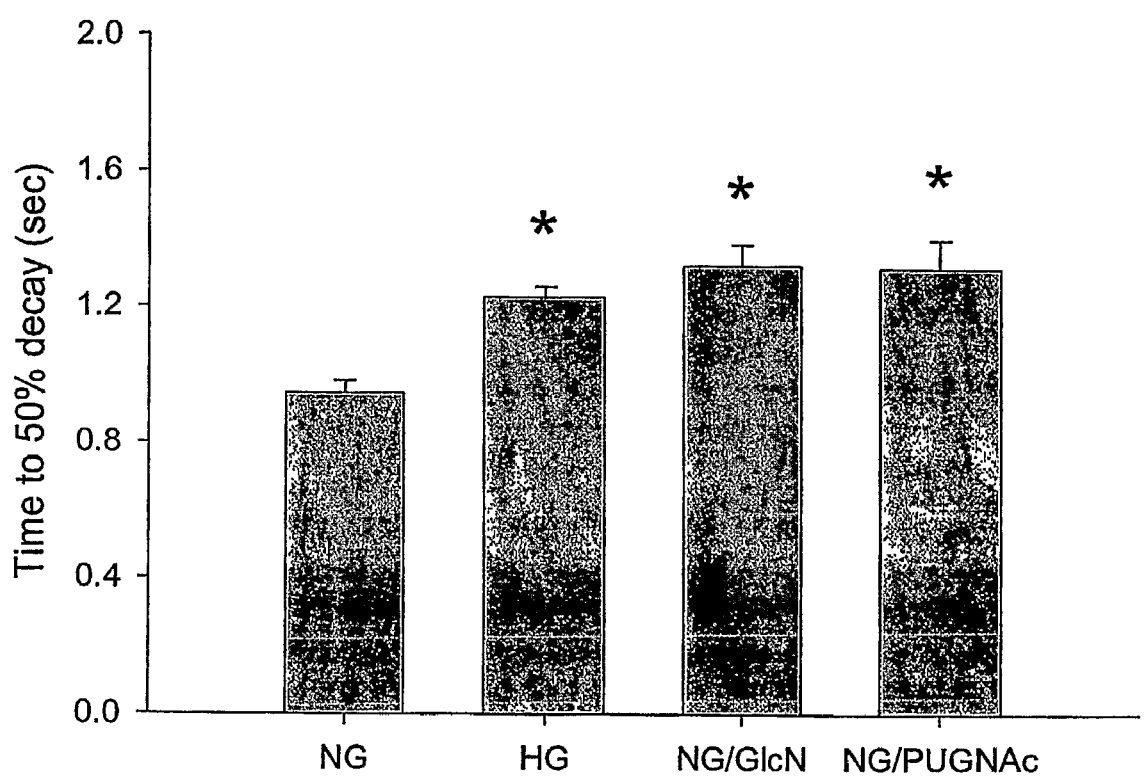
Figure 1C:
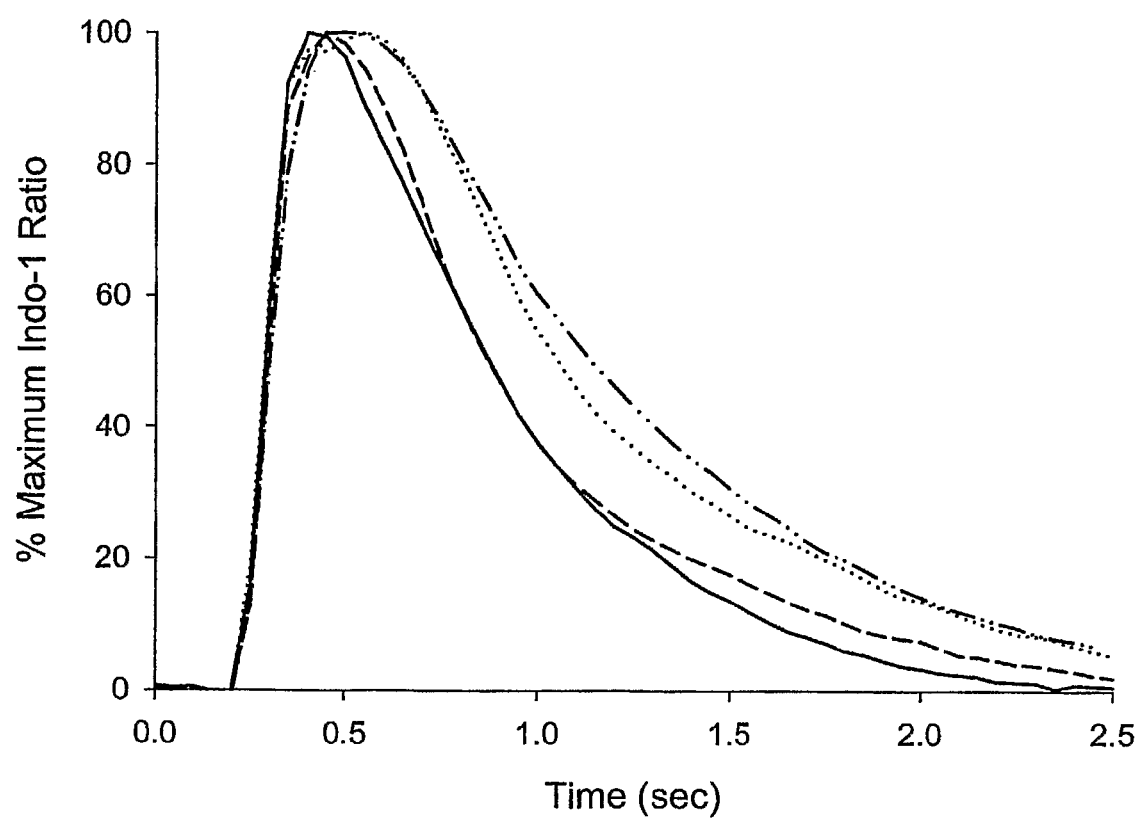

FIGS. 1A and 1C illustrate typical traces from these experiments. FIGS. 1A and 1C illustrate calcium transients measured in neonatal cardiomyocytes that were, inter alia, exposed to high glucose and infected with either adenovirus encoding O-GlcNAc transferase or O-GlcNAcase. Intracellular $Ca^{2+}$ transients in neonatal cardiomyocytes measured using Indo-1 fluorescence as described in "Experimental Procedures" above. Cells (0.5×10⁶/plate) were incubated for 72 hours in either (A) 5.5 mM glucose (NG, solid line) or 25 mM glucose (HG, dotted line), normal glucose supplemented with 8 mM glucosamine (GlcN, dashed line), or normal glucose treated with 50 μM PUGNAc (dashed and dotted line), or (C) normal glucose (solid line), high glucose (dotted line), and high glucose infected with either adenovirus encoding O-GlcNAc transferase (OGT, dashed and dotted line) or O-GlcNAcase (GCA, dashed line). Cells were loaded with Indo-1/AM and Indo-1 ratios were normalized relative to the baseline and the maximum of each trace set to 100%. Data represents the mean of 18 myocytes for each treatment, and experiments were performed using cultured cells from three separate isolations. (B and D) Graphical representation of the time to 50% decay of the calcium transient ($T_{1/2}$) based on the data presented in 1A (B) or 1C (D). An * indicates a statistically significant (P<0.05) difference compared with myocytes cultured in 5.5 mM glucose.

Figure 1D:
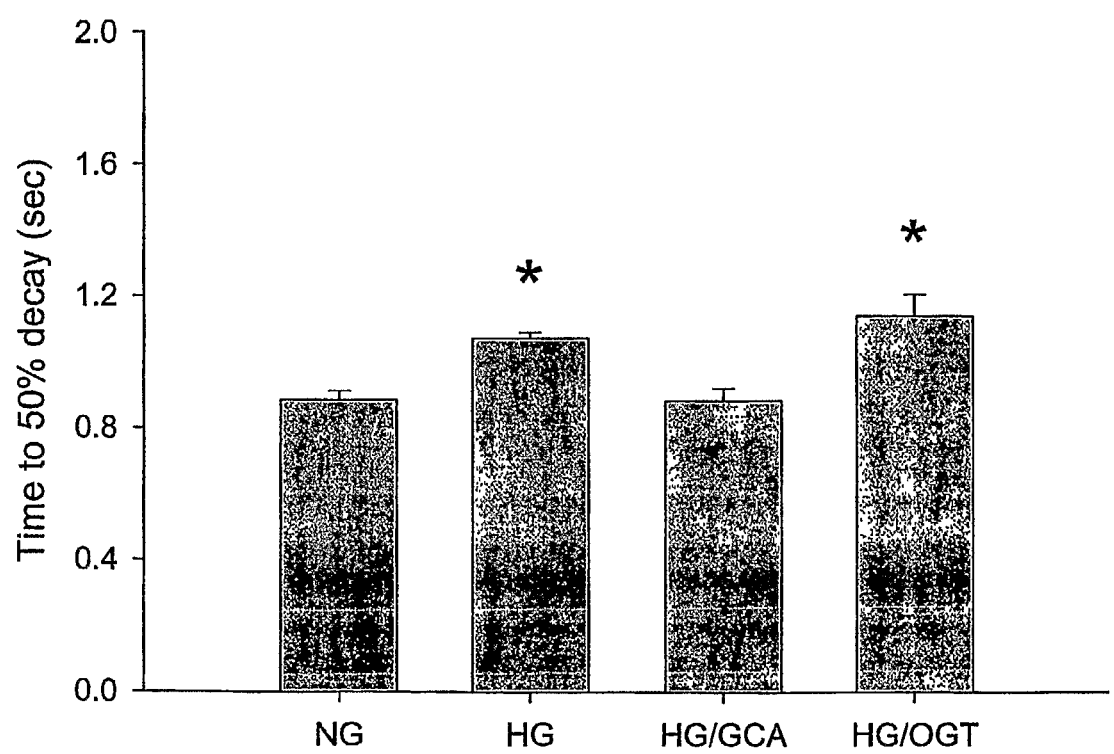

Treatment of myocytes with 5.5 mM or 25 mM glucose resulted in similar kinetics for achieving peak Indo-1 ratios during systole, but the diastolic decay phase was significantly prolonged in myocytes exposed to high glucose. The time to achieve a 50% decrease in the calcium transient ($T_{1/2}$) in normal and high glucose-treated myocytes was 914±31 and 1149±24 msec, respectively, and represents a 26% slower $T_{1/2}$ in the latter group (P<0.01; FIG. 1B). Exposing myocytes to treatments designed to increase nucleocytoplasmic GlcNAcylation further prolonged the $T_{1/2}$ and suggested a trend, albeit not significantly beyond high glucose treatment, toward slower systolic kinetics. Treatment of myocytes with 5.5 mM glucose supplemented with either 8 mM glucosamine or 50 μM PUGNAc increased $T_{1/2}$ to 1320±61 and 1310±85 msec, respectively (FIG. 1B), which corresponds to a 43% increase in diastolic calcium decay for both treatments relative to controls (P<0.01). Infection of myocytes with adeno-SR (control virus), adeno-GCA or adeno-OGT had no significant effect on normal glucose-treated myocytes, but adeno-OGT infected cells exposed to 25 mM glucose exhibited prolonged $T_{1/2}$ (1213±86) that was similar to treatment with glucosamine (FIG. 1C/D). Infection of high glucose-treated myocytes with adeno-GCA resulted in a reduced $T_{1/2}$ that was similar to controls (FIG. 1D).

Figure 2:
FIG. 2A and FIG. 2B illustrate Northern and western blots of neonatal cardiomyocytes under experimental conditions as described in detail in Example 1, below.
FIG. 2C illustrates results using myocytes with adenovirus encoding either OGT or GCA, also as described in detail in Example 1, below.
Figure 2:
Figure 2:

SERCA2a in RNA, protein expression and promoter activity. Northern blot analysis of mRNA extracted from myocytes demonstrated a substantial decrease in SERCA2a mRNA with exposure to 25 mM glucose compared with normal glucose-treated cells (−37±6%; P<0.05; FIG. 2A). FIG. 2 illustrates Northern and western blots of neonatal cardiomyocytes. (FIG. 2A) Results of a northern blot for SERCA2a mRNA in neonatal cardiomyocytes cultured for 72 hours with 5.5 mM (NG) or 25 mM (HG) glucose. Total RNA (15 μg) isolated from cultured myocytes was resolved using a denaturing agarose gel, transferred to a nylon membrane and probed with a full length $^{32}P$-labeled probe corresponding to rat SERCA2a as described in "Experimental Procedures". (FIG. 2B) Western immunoblot analysis of SERCA2a protein levels from neonatal cardiomyocytes exposed to 5.5 mM or 25 mM glucose in the presence and absence of 40 μM aminoguanidine (AG), 0.5 μg/ml tunicamycin (Tun), or 8 mM glucosamine (GlcN, 5.5 mM glucose group only). Crude lysates (30 μg) were resolved using 4-20% gradient SDS-PAGE gels, transferred to nylon membranes, and immunoblotted with a SERCA2a polyclonal antibody as described in "Experimental Procedures". The apparent increase in SERCA2a in cells treated with 25 mM glucose and aminoguanidine is not statistically significant from controls with repeated trials. (C) SERCA2a protein levels based on Western immunoblots from adenovirus-infected neonatal cardiomyocytes. Cells were cultured in either NG or HG glucose and infected at an MOI of 25 with adeno-OGT, adeno-GCA, or empty virus (SR−).

The decrease in SERCA2a mRNA with high glucose treatment paralleled a similar decrease in SERCA2a protein (−28±4%; P<0.01; FIG. 2B). To examine the role of specific glycosylation pathways, myocytes were incubated in 40 µM aminoguanidine (an inhibitor of non-enzymatic glycosylation), 0.5 µg/ml tunicamycin (an inhibitor of N-linked glycosylation), or 8 mM glucosamine. Cells exposed to both 5.5 mM glucose and 8 mM glucosamine exhibited a significant decrease (−25±3%; P<0.01) in SERCA2a protein compared with controls (FIG. 2B). Interestingly, SERCA2a protein levels in myocytes exposed to both 25 mM glucose and glucosamine were unchanged compared with myocytes exposed only to 5.5 mM glucose. This effect was observed reproducibly but we cannot explain it satisfactorily. Neither aminoguanidine nor tunicamycin appeared to influence SERCA2a protein levels regardless of glucose concentration (FIG. 2B), nor did we observe any osmotic effect when cells were treated with 5.5 mM glucose and a cell-impermeable osmotic carrier (20 mM mannitol).

To examine specifically the effect of increased O-GlcNAcylation on SERCA2a protein expression, we infected myocytes with adenovirus encoding either OGT or GCA at a (MOI) of 25. Treatment of myocytes with high glucose and adeno-OGT resulted in a 47±9% decrease in SERCA2a protein expression compared with control cells infected with an empty adenovirus (SR−; FIG. 2C). Importantly, infection of high glucose-exposed myocytes with adeno-GCA resulted in remarkably improved SERCA2a protein levels (FIG. 2C).

Figure 3:
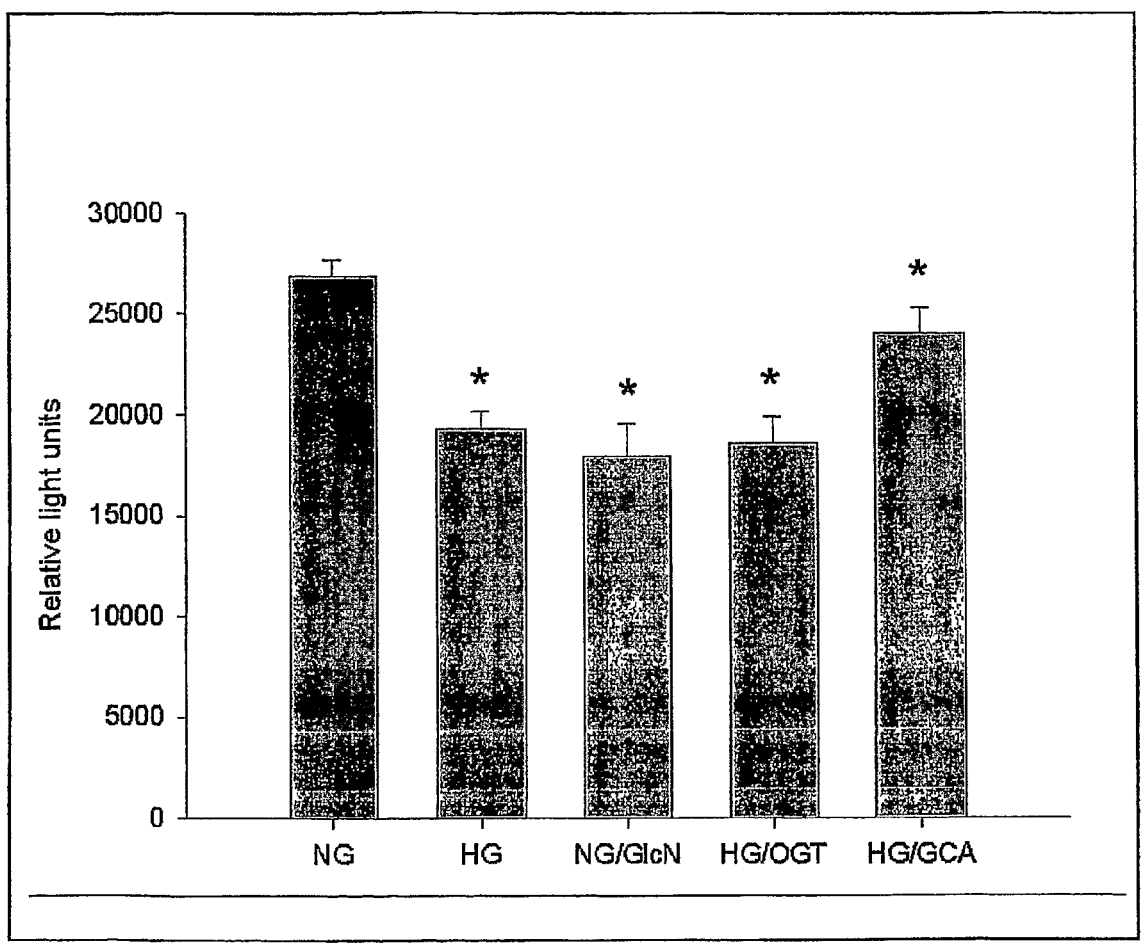
FIG. 3 illustrates luciferase assays for sarcoendoplasmic reticulum $Ca^{2+}$ ATPase (SERCA2a) promoter activity in myocytes exposed to either various amounts of glucose or glucose and glucosamine, as described in detail in Example 1, below.

The reduction in SERCA2a mRNA and protein expression observed following treatment of myocytes with high glucose prompted us to examine whether these effects were being exerted, at least in part, by interactions with the SERCA2a gene promoter. Cells were transfected with a 0.6 kb fragment of the rat SERCA2a promoter inserted into the luciferase vector, pGL3 (Promega). Luciferase assays indicated that myocytes exposed to either 25 mM glucose or 5.5 mM glucose/8 mM glucosamine exhibited a significant reduction in SERCA2a promoter activity (28% and 33%, respectively; P<0.01) compared with normal glucose controls, see FIG. 3, illustrating luciferase assays for SERCA2a promoter activity. Neonatal cardiomyocytes were cultured in either 5.5 mM (NG) or 25 mM (HG) glucose media, and chemically-transfected with a 0.6 kb fragment of the rat SERCA2a promoter in pGL3 as described in "Experimental Procedures". To determine the effects of altering cellular glycosylation specifically, cells were further treated with 8 mM glucosamine (NG/GlcN) or adenoviruses encoding either O-GlcNAc transferase (HG/OGT) or O-GlcNAcase (HG/GCA) for 48 hours prior to chemical transfection with the SERCA2a promoter construct glycosylation. Crude cell lysates were incubated with luciferase substrate and relative light units were measured on a luminometer. An (*) indicates a significant difference (P<0.05) existed between an experimental group and the control (NG).

Overexpression of OGT had no effect on SERCA2a promoter activity in control cells, but we measured considerably reduced promoter activity in high glucose-treated cells infected with adeno-OGT (31%; P<0.01; FIG. 3). Exposing myocytes to adeno-GCA and high glucose resulted in improved SERCA2a promoter activity, albeit activity did not return to control levels. Infection of myocytes with control virus had no effect on SERCA2a promoter activity relative to uninfected controls.

Figure 4:
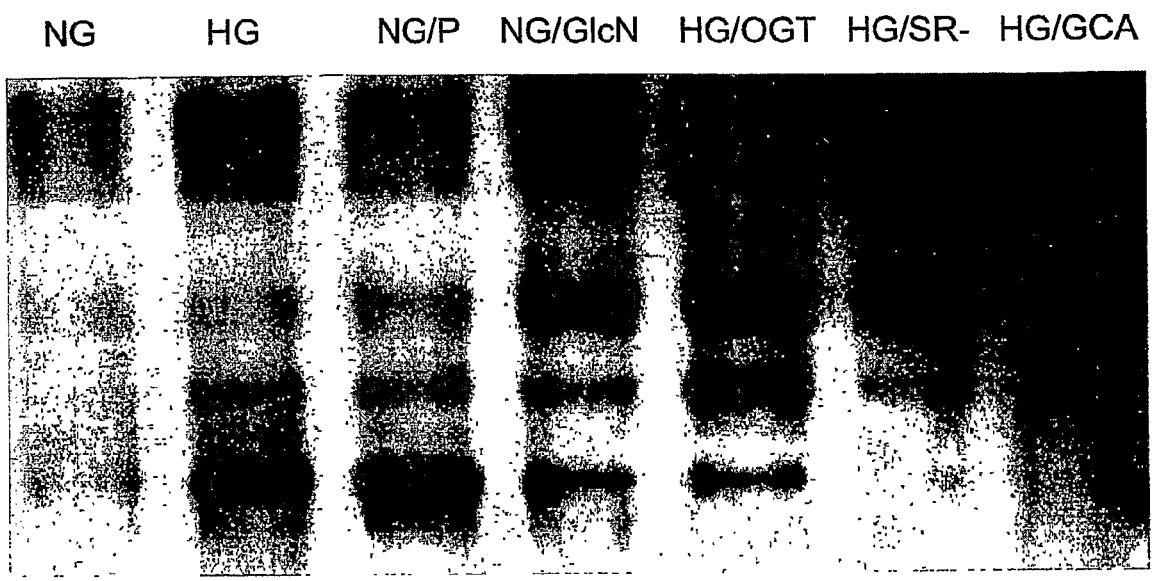
FIG. 4 illustrates Western immunoblot effects of various treatments (e.g., varying glucose levels) on nuclear O-glycosylation in cultured neonatal cardiomyocytes, as described in detail in Example 1, below.

Effects of nuclear O-GlcNAcylation. The effects of 25 mM glucose and adeno-OGT treatment on myocytes suggested that increased O-GlcNAcylation was affecting transcriptional activity in the cell. Because numerous transcription factors interact with the SERCA2a promoter and other elements of myocardial Ca$^+$ cycling), we examined whether the overall level of O-GlcNAcylation was altered in nuclear extracts from cardiomyocytes. The monoclonal antibody 110.6 recognizes the O-linkage of a single N-acetylglucosamine molecule to serine/threonine residues (see, e.g., Comer (2001) Anal. Biochem. 293:169-177) and thus provides a useful tool for examining the GlcNAcylation status of nuclear proteins. Our results revealed that overall levels of nuclear O-GlcNAcylation were substantially increased in myocytes exposed to 25 mM glucose, 5.5 mM glucose supplemented with either 8 mM glucosamine or 50 µM PUGNAc, or 25 mM glucose and infected with adeno-OGT (FIG. 4). Infection of high glucose-treated cells with adeno-GCA resulted in a significant reduction in overall cellular O-GlcNAcylation, see FIG. 4. No such changes in O-GlcNAcylation were observed when myocytes were incubated with control virus (data not shown). FIG. 4 illustrates Western immunoblot effects of various treatments (e.g., varying glucose levels) on nuclear O-glycosylation in cultured neonatal cardiomyocytes. Cells were cultured for 72 hours in 5.5 mM glucose (NG) or 25 mM glucose (HG) and supplemented with one of the following: 8 mM glucosamine (NG/GlcN), 50 µM PUGNAc, or adenovirus encoding either OGT or GCA. Adenoviruses were applied at an MOI=25. Nuclear extracts (50 µg) were prepared according to the methods outlines in "Experimental Procedures", resolved on 4-20% gradient SDS-tricine gels, transferred to nylon membranes and immunoblotted with a monoclonal anti-O-GlcNAc antibody 110.6.

Effects on Sp1 and MEF2 expression and glycosylation. The inhibitory effects of high glucose treatment and elevated nucleocytoplasmic O-GlcNAcylation on SERCA2a expression and promoter activity prompted us to examine a possible molecular mechanism linking increased glycosylation directly to alterations in SERCA2a expression. The transcription factor Sp1 contains sites that are modified specifically by O-GlcNAcylation, and the SERCA2a promoter contains several Sp1 recognition sequence sites. To investigate whether hyperglycemia could influence Sp1, we exposed myocytes to 5.5 mM glucose, 25 mM glucose, or high glucose and adeno-OGT and isolated Sp1 by immunoprecipitation.

Our results indicate that levels of Sp1 protein were unchanged in myocytes exposed to either 25 mM glucose, with or without adeno-OGT, compared with normal glucose-treated cells (FIG. 5A). However, these treatments substantially increased levels of Sp1 O-GlcNAcylation (FIG. 5B). Incubation with control virus had no effect on Sp1 expression or glycosylation regardless of the glucose concentration of the media.

Figure 5:
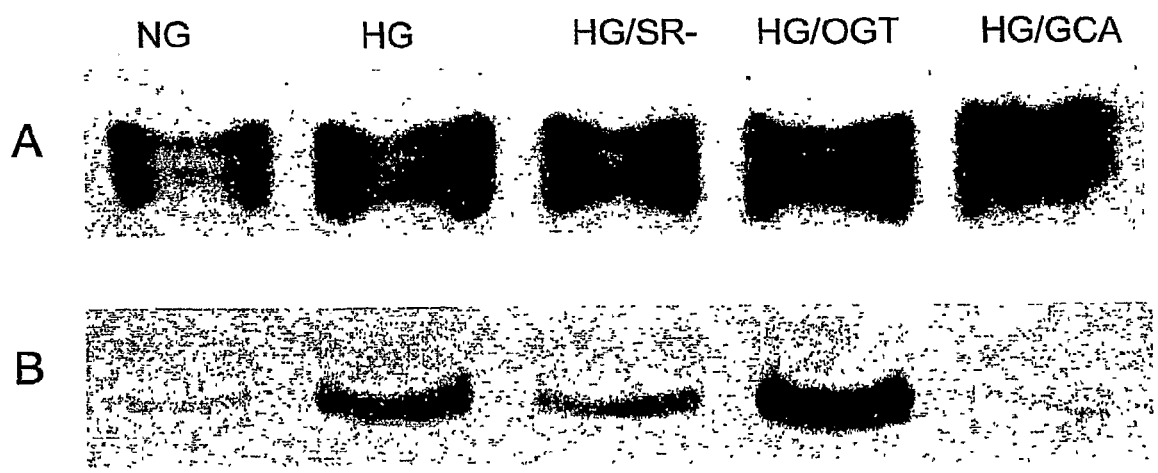
FIG. 5A and FIG. 5B illustrate levels of specificity protein 1 ("Sp1") protein (by Sp1 immunoprecipitation) in myocytes exposed to either glucose with or without adeno-OGT as compared with normal glucose-treated cells, as described in detail in Example 1, below.

FIG. 5 illustrates Sp1 immunoprecipitation from cultured neonatal cardiomyocytes. Cells were cultured for 72 hours in experimental medium (NG, HG, or HG with either adeno-OGT or adeno-GCA). Sp1 was immunoprecipitated from nuclear extracts (50 µg) as described in "Experimental Procedures" above, resolved electrophoretically on 7.5% SDS-PAGE gels, transferred to nylon membranes and immunoblotted with polyclonal antibodies to either Sp1 (A) or O-glycosylated residues (B) (anti-O-GlcNAc antibody 110.6).

Figure 6:
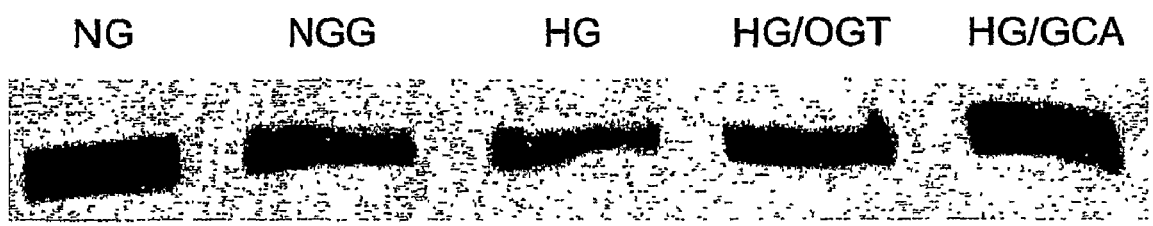
FIG. 6 illustrates MEF-2 (myocytes enhancer factor-2) protein levels from cultured rat neonatal cardiomyocytes incubated in either glucose or glucose with or without, inter alia, glucosamine, adeno-OGT or adeno-GCA, as described in detail in Example 1, below.

Although the MEF-2 transcription factor is not known to be subject to O-GlcNAcylation, it is nevertheless important for the expression of a variety of essential proteins in cardiomyocytes, including SERCA2a (see, e.g., Moriscot (1997) Endocrinology 138:26-32). To examine whether elevated glucose could affect MEF-2 levels, we exposed myocytes to 5.5 mM or 25 mM glucose, and supplemented with each of the following: 8 mM glucosamine, adeno-OGT, or adeno-GCA. Results from immunoblots of nuclear extracts indicated that MEF2a expression was decreased considerably by treatments that increased overall levels of nuclear glycosylation, as illustrated in FIG. 6. FIG. 6 illustrates MEF-2 protein levels from cultured rat neonatal cardiomyocytes. Cells were incubated in either 5.5 mM glucose (NG) or 25 mM glucose (HG) with or without the following: 8 mM glucosamine, adeno-OGT or adeno-GCA (MOI=25). Nuclear extracts (50 μg) were prepared as described in "Experimental Procedures" above, resolved on 10% SDS-PAGE gels, transferred to nylon membranes and immunoblotted with anti-MEF2 antibody (Santa Cruz Biotech).

Specifically, as illustrated in FIG. 6, treatment with 25 mM glucose, 5.5 mM glucose supplemented with 8 mM glucosamine, or 25 mM glucose and infected with adeno-OGT resulted in 49%, 52%, and 41% decreases in MEF-2a expression levels, respectively, compared with normal glucose controls. Infection of high glucose-exposed myocytes with adeno-GCA restored MEF-2a levels to near-normal levels. Infection with empty adenovirus had no effect regardless of glucose concentration. We observed no evidence of O-GlcNAcylation of MEF-2a protein.

Figure 7A:
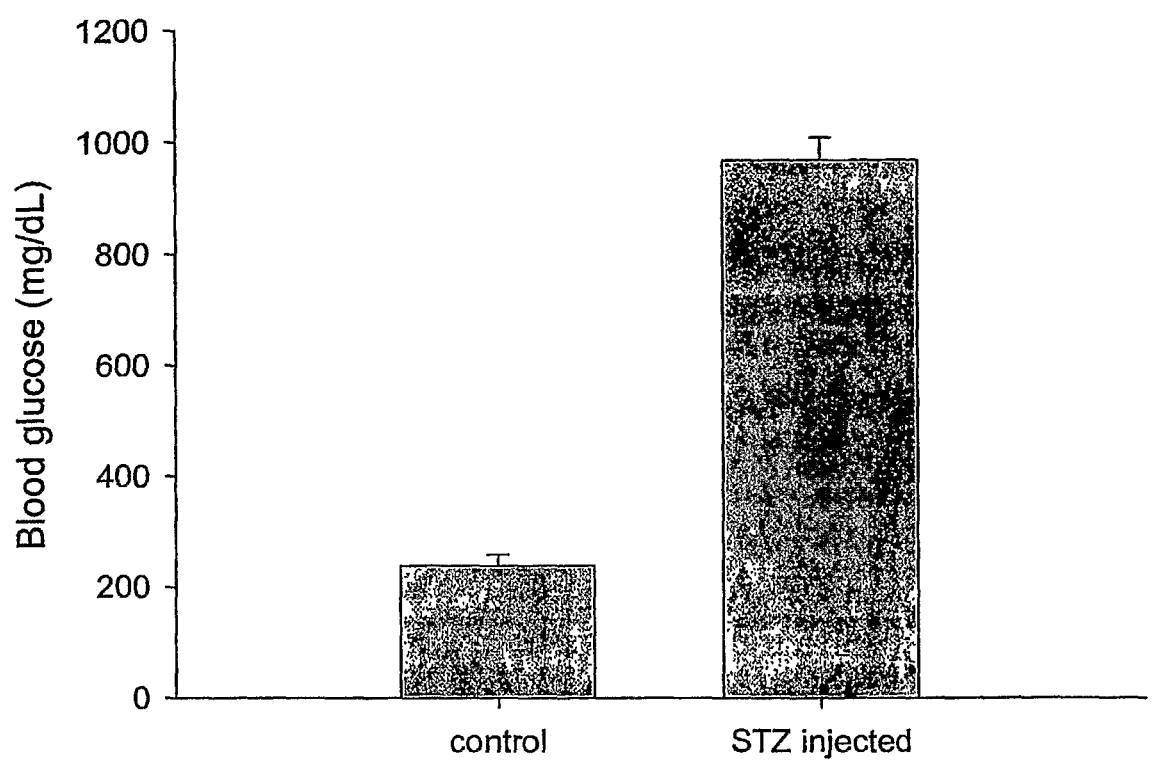
FIG. 7 illustrates blood glucose and UDP-nucleotide concentrations in control and diabetic mice, as described in detail in Example 1, below.
Figure 7B:
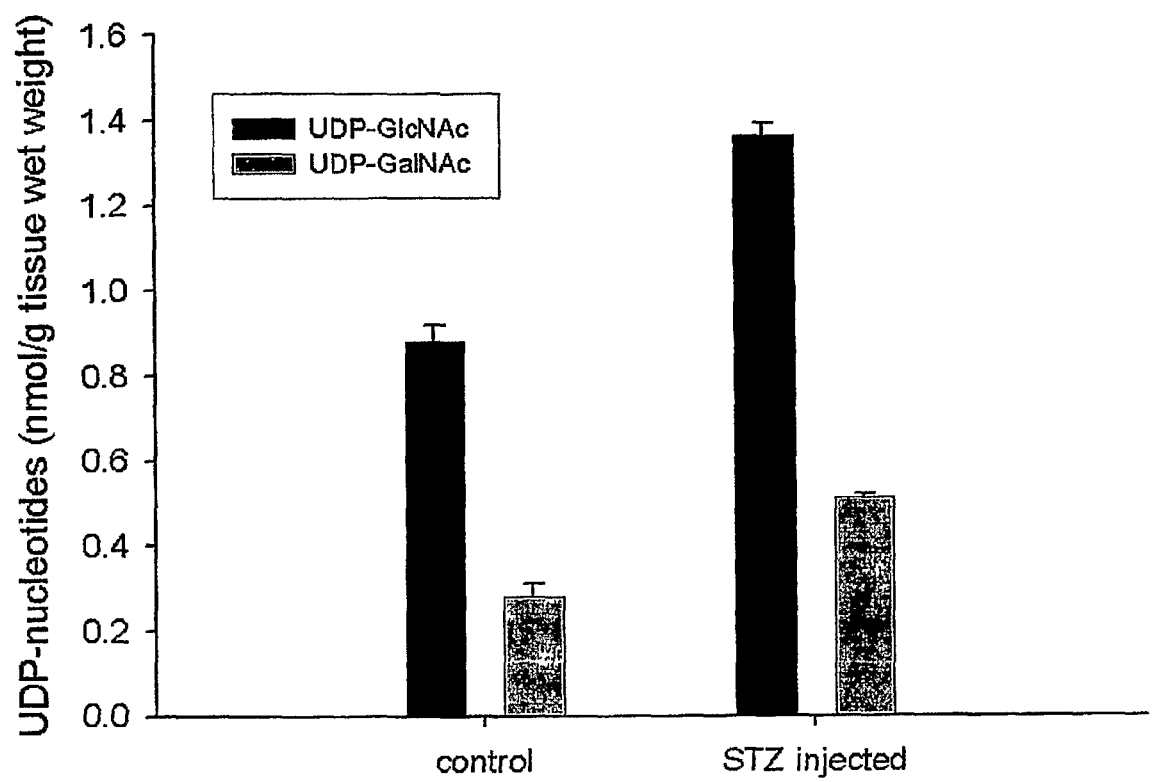

Effects of STZ-induced diabetes on UDP-nucleotide levels. To provide for a possible mechanism linking diabetic hyperglycemia to substrate flux through the hexosamine pathway, we examined concentrations of sugar nucleotides (UDP-GlcNAc and UDP-GalNAc) in hearts from animals made diabetic by injection with streptozocin (STZ), as illustrated in FIG. 7, which illustrates blood glucose and UDP-nucleotide concentrations in control and diabetic mice. Mice (20-25 g) were injected intraperitoneally with streptozocin (150 mg/kg) and subsequently developed diabetes over a three week period. Blood was drawn via direct cardiac puncture and plasma [glucose] was subsequently determined using a Sigma Glucose kit. Sugar nucleotides were extracted immediately from hearts and quantitated using HPLC as described in "Experimental Procedures" above. UDP-GlcNAc and UDP-GalNAc were collected in a single fraction via HPLC using a Mono-Q column, then separated into individual fractions using a PARTISIL SAX-10™ column. Fractions were quantified by comparing total peak area with results from known concentrations of each sugar nucleotide.

STZ-injected animals exhibited severe hyperglycemia relative to controls ([blood glucose]=969±40 vs. 238±20 mg/dL, respectively). Diabetic animals also exhibited elevated levels of both UDP-GlcNAc and UDP-GalNAc compared with control animals (1.36±0.03 and 0.51±0.01 nmol in diabetic animals vs. 0.88±0.04 and 0.28±0.03 nmol in controls, respectively).

Discussion

In this study we demonstrate that exposure of cells to high extracellular glucose concentrations ([Glc]$_o$) can lead to impaired diastolic calcium sequestering, and this appears to occur through a high [Glc]$_o$-induced reduction in SERCA2a expression. While the invention is not limited by any particular mechanism of action, the invention also provide for a possible mechanism for these perturbations in contractile function and calcium homeostasis with the observations that increased O-GlcNAcylation is sufficient to alter SERCA2a expression, at least in part through effects on nuclear transcription factors. Accordingly, these studies demonstrate that the compositions and methods of the invention can be effective for reducing O-GlcNAcylation, "normalizing" SERCA2a activity and enzyme levels in hyperglycemic conditions, and improving myocyte contractile function and calcium homeostasis under hyperglycemic conditions.

Treatment of adult rat ventricular cardiomyocytes with elevated [Glc]$_o$ has been shown recently to result in prolonged action potential duration, impaired diastolic calcium uptake, and poor contractile performance (see, e.g., Ren (1997) Am. J. Physiol. 273:H2876-2883). These effects are similar to impaired cardiomyocyte function observed in myocytes isolated from diabetic animals, as described, e.g., in Lagadic-Gossmann (1996) Am. J. Physiol. 270:H1529-1537. The studies presented herein support and extend these observations by demonstrating that neonatal rat cardiomyocytes exposed to elevated [Glc]$_o$ exhibit prolonged calcium transients, and that the observed diastolic impairment in calcium flux can be linked to reduced expression of the SERCA2a. SR calcium release and subsequent re-uptake serve as the primary determinants of myocardial systolic contraction and diastolic relaxation, respectively. The rate of calcium sequestration into the SR is controlled by SERCA2a, which also affects total SR calcium storage (see, e.g., Periasamy (2001) J. Mol. Cell. Cardiol. 33:1053-1063). A reduction in the expression of SERCA2a would likely result in a decreased rate of calcium reuptake and lead to prolonged calcium transients. The results of our experiments agree with observations we reported recently demonstrating that hearts from STZ-induced diabetic mice express reduced levels of SERCA2a protein, and that the contractile deficits observed in these animals could be rescued in transgenic mice expressing SERCA2a and made diabetic (see Trost (2002) supra).

Diabetic hyperglycemia can exert detrimental effects on the myocardium via several mechanisms, but increased attention is being focused on the hypothesis that increased glucose flux through the hexosamine biosynthetic pathway plays an important role in the pathogenesis of diabetes (see, e.g., Marshall (1991) supra). Under normal conditions approximately 2-3% of glucose entering the cardiomyocyte is shunted to the hexosamine pathway (Marshall (1991) supra). Upon initial examination, it may seem counterintuitive that excess glucose may be available for hexosamine biosynthesis despite the relative glucose insensitivity of diabetic tissues. However, despite either reduced insulin levels or insulin resistance, elevated [Glc]$_o$ may still enter the myocyte via the glucose transporter Glut1, which is less insulin sensitive than Glut4 (see, e.g., Zorzano (1997) Am. J. Cardiol. 80:65A-76A). Furthermore, low or absent insulin levels in the diabetic milieu will impair glucose flux through glycolysis and glycogen synthesis, potentially shunting glucose to alternative metabolic pathways such as the hexosamine pathway, or for the non-enzymatic glycation of cellular proteins. Although measurements of glucose flux rates into hexosamine biosynthesis has not been measured in cardiomyocytes from diabetic animals, our results clearly demonstrate that hearts from diabetic mice exhibit elevated concentrations of UDP-GlcNAc, an important common substrate for both N- and O-linked glycosylation. Indeed, dysfunctional calcium cycling in diabetic hearts may be predicated, in part, on an increase in UDP-GlcNAc levels, as suggested by our observation that adeno-OGT infection had no effect on myocytes incubated in normal glucose (i.e., OGT activity is limited by substrate availability). The observed decrease in SERCA2a expression we observed in neonatal cardiomyocytes exposed to elevated [Glc]$_o$ does not appear to occur as a result of increased non-enzymatic glycation or N-linked glycosylation. This latter result is in direct contrast to the apparent amelioration of contractile performance and calcium homeostasis observed in adult rat myocytes exposed to elevated [Glc]$_o$ and treated with tunicamycin (see Ren (1997) supra). We are uncertain why this difference exists. Instead, our results suggest that the abnormalities in cardiomyocyte calcium flux result from enhanced O-GlcNAcylation of cellular proteins, and in particular an increase in the O-linkage of N-acetylglucosamine molecules on target proteins.

Considerable evidence indicates that hyperglycemia and elevated $[Glu]_o$ can affect gene expression in cardiac and non-cardiac tissue (see, e.g., Cagliero (1988) J. Mol. Cell. Cardiol. 20:427-434; Dillmann (1988) Diabetes Metab. Rev. 4:789-797; McClain (1992) Proc. Natl. Acad. Sci. USA 89:8150-8154). Furthermore, it is known that dynamic O-GlcNAcylation modifies the activity and function of RNA polymerases, cytoskeletal proteins, and transcription factors (see, e.g., Hart (1997) Annu. Rev. Biochem. 66:315-335; Wells (2001) Science 291:2376-2378). Recent reports demonstrate that the transcription factor Sp1 is subject to dynamic O-GlcNAcylation, and that this modification results in decreased transcriptional activity of the protein (see, e.g., Yang (2001) Proc. Natl. Acad. Sci. USA 98:6611-6616; Yang (2002) Cell 110:69-80).

The SERCA2a promoter contains multiple Sp1 binding sites which are important for adequate gene expression; we investigated the nexus of these cellular mechanisms. Our results provide clear evidence that the effects of hyperglycemia on cardiac function, and SERCA2a expression in particular, may be transmitted through effects on the transcription factor Sp1. The significant increase in Sp1-specific O-GlcNAcylation provides for a molecular mechanism that, for the first time, links hyperglycemia, increased hexosamine flux, and the transcriptional regulation of SERCA2a expression, with cardiomyocyte dysfunction in the diabetic context.

Finally, this study demonstrates for the first time that the removal of O-GlcNAc residues is sufficient, in most cases, to normalize cardiomyocyte function despite exposure to hyperglycemia. Virally-transmitted O-GlcNAcase was sufficient to improve diastolic calcium handling and to elevate SERCA2a levels and promoter activity to near normal levels in cells exposed to conditions that otherwise result in increased cellular O-GlcNAcylation and a subsequent reduction in function. Thus, these studies demonstrate that the compositions and methods of the invention, utilizing an O-GlcNAcase gene in gene therapy, e.g., a virally-encoded O-GlcNAcase gene, are effective to counteract the detrimental effects of elevated extracellular glucose. Thus, these studies demonstrate that the compositions and methods of the invention provide an effective gene therapy approach to address (treat, ameliorate and/or prevent) cardiac dysfunction in diabetic patients.

In summary, the invention for the first time demonstrates that elevated extracellular glucose impairs calcium cycling in cardiomyocytes and that these changes appear through increased cellular O-GlcNAcylation. We have also observed that the detrimental effect of increased cellular O-GlcNAcylation can be mitigated against through increased expression of O-GlcNAcase in the cells. Increased expression of O-GlcNAcase was accomplished through use of transfection of the cells with an adenovirus vector encoding the protein. Thus, we have discovered methods and agents for treating cardiomyopathy associated with diabetes.

The present invention provides methods for ameliorating a symptom of diabetic cardiomyopathy in a subject in need thereof by decreasing the cellular O-GlcNAcylation in the cardiomyocytes. Thus, the invention provides methods for increasing contractile function in the heart of a subject with diabetes. The invention also provides methods for increasing myocardial performance in a subject with diabetes. The desired decrease in cellular O-GlcNAcylation may be attained in a number of ways, including, but not limited to, through an increase in O-GlcNAcase in the cells. The compositions and methods of the invention provide agents that increase O-GlcNAcase activity in cells, e.g., myocytes. For example, expression constructs, e.g., vectors, encoding O-GlcNAcase are used, and in one aspect are introduced and expressed in cells. In one aspect, viral, e.g., adenoviral or lentiviral, expression vectors for transfecting cardiomyocytes are effective for increasing O-GlcNAcase activity in transfected cardiomyocytes. In another aspect, the invention provides screening methods for identifying agents for use in treating diabetic cardiomyopathy through characterizing the agents effect on cellular O-GlcNAcylation.

Example 2

Adenovirus Mediated Overexpression of O-GlcNAcase Improves Contractile Function in the Diabetic Heart The following example describes making and using exemplary compositions and methods of the invention. The data presented herein demonstrate, inter alia, that the compositions and methods of the invention are effective for treating or ameliorating (or preventing) cardiomyopathies such as diabetic cardiomyopathy. Using in vivo adenovirus-mediated gene delivery to the heart, we overexpressed GCA in STZ-induced diabetic mice and evaluated the effects of reducing cellular O-GlcNAcylation on diabetic cardiac dysfunction and demonstrated using exemplary compositions and methods of the invention that overexpression of O-GlcNAcase improves contractile function in the diabetic heart.

Materials and Methods

Preparation of Diabetic Mice:

NIH Swiss mice (25 g) were made diabetic by a single i.p. injection with freshly prepared streptozotocin (STZ) solution (200 mg/kg body weight in citrate saline, pH 4.2) after overnight fasting, as described, e.g., e.g., Trost (2002) Diabetes 51:1166-1171. The diabetic status was assessed by measuring urine glucose (>22 mmol/L=diabetic) 3 days after STZ-injection and was confirmed by blood glucose measurement at the time of sacrifice.

To rule out any potentially toxic effects of STZ on the heart, several STZ-injected mice were intensively treated with Ultralente human insulin (Eli Lilly and Company, IN) with 50 units/g per day subcutaneously. The insulin treatment commenced on the third day after STZ injection and lasted for 2 weeks. The cellular O-GlcNAcylation in these hearts was compared with that of the non-insulin treated diabetic hearts. In addition, several 20 weeks old male polygenic diabetic NONcNZO10/LtJ mice (The Jackson Laboratory) (see, e.g., Reifsnyder (2002) Diabetes 51:825-832; Leiter (2004) Diabetes 53 Suppl 1:S4-11) were used as a type II diabetic model to investigate the excess O-GlcNAcyaltion level in the diabetic heart independent of STZ administration. These mice developed hyperglycemia at 12-16 weeks. At the sacrifice time, blood glucose levels were above 33.3 mmol/L. Animal procedures were performed in accordance with the guidelines established by the Committee on Animal Research at the University of California, San Diego.

In vivo adenoviral gene delivery: In vivo adenovirus gene delivery in diabetic mice was performed as previously described, e.g., by Suarez (2004) Am. J. Physiol. Heart Circ. Physiol. 286:H68-75. Either adenovirus encoding human GCA (Adv-GCA) or adenovirus without encoding gene sequence (Adv-SR−) was directly injected into the left ventricular wall (five sites, 10 μl of $10^{10}$ pfu/ml each). In the experiments involving individual myocyte studies, a green fluorescent protein expressing adenovirus (Adv-GFP) was co-injected to help identify either Adv-GCA or Adv-SR− infected myocytes after myocytes isolation (Suarez (2004)

supra). Another group of normal age-matched NIH Swiss mice receiving Adv-SR– was used as a control group in some series of experiments.

Measurement of $Ca^{2+}$ transients and sarcoplasmic reticulum calcium load: Single ventricular myocytes were enzymatically isolated and $Ca^{2+}$ transients were measured as previously described by, e.g., Suarez (2004) supra; Giordano (1997) Circulation 96:400-403. Only those myocytes infected with Adv-GCA or Adv-SR– (as indicated by GFP fluorescence) were studied. $Ca^{2+}$ transients were recorded from at least 20 cells per heart and for at least 3 hearts per treatment. Diastolic and systolic intracellular $Ca^{2+}$ levels were inferred from the basal and maximal indo-1 ratio per cycle, respectively. Diastolic decay time ($T_{decay}$) was calculated from the normalized $Ca^{2+}$ transient curve.

Sarcoplasmic reticulum calcium load was measured as described by, e.g., Shannon (2002) Circ Res. 91:594-600. In brief, cells were superfused with normal Tyrode's solution (1 mmol/L $Ca^{2+}$) and paced at 0.3 Hz to steady state. The solution was then rapidly switched to a $Na^+$- and $Ca^{2+}$-free Tyrode solution with a rapid solution exchanger device. After 20 seconds (s), cells were rapidly exposed to 10 mmol/L caffeine (in $Na^+$- and $Ca^{2+}$-free Tyrode's solution). The difference between the basal and peak $Ca^{2+}$ transient induced by caffeine was used as an index of sarcoplasmic reticulum $Ca^{2+}$ load.

Measurement of myocyte contractility by edge detection: The contractile properties of single myocytes were measured using edge detection as described, e.g., by He (1999) Circulation 100:974-980. Myocyte fractional shortening, maximal shortening rate (+dL/dt) and relengthening rate (–dL/dt) were analyzed with Felix32 software (Photon Technology International Inc.). Again, only infected myocytes as indicated by GFP signal were studied. Data were collected from at least 10 cells per heart and 3 hearts per treatment.

Measurement of ventricular function by isolated perfused hearts: Diabetic mice were randomly divided into two groups, with each receiving either Adv-GCA or Adv-SR– via in vivo adenovirus gene delivery. Five days following the procedure, hearts were isolated and Langendorff-perfused for functional analysis as previously described, e.g., by Trost (1998) J. Clin. Invest. 101:855-62; Suarez (2004) supra. The hearts were paced at 400 beats/min, and the resulting pressure waves were analyzed for pressure derivatives [rate of contraction (+dP/dt), rate of relaxation (–dP/dt)] and developed pressure. Another set of normal mice served as a non-diabetic control group and underwent the same procedure. At the end of the experiment, hearts were frozen in liquid $N_2$ for Western blot analysis.

RNase Protection assay: RNase protection assays were performed as previously described by, e.g., Gloss (2001) Endocrinology 142:544-550. The human GCA (hGCA) probe spans residues 1035-1143 in the published human cDNA sequence (NM_012215), and the mouse GCA (mGCA) probe spans residues 881-1020 in the published mouse sequence (AF132214). The mouse OGT probe spans residues 57-215 in the published sequence (AF363030), which yields a 159 bp signal for full length OGT nucleocytoplasmic isoform (ncOGT) and a 150 bp signal for the OGT mitochondrial isoform (mitOGT).

Western Immunoblotting: Cytosolic and nuclear fractions were prepared by differential centrifugation. Cardiac tissues were homogenized with a POLYTRON™ homogenizer in a buffer containing 30 mmol/L Tris, 300 mmol/L sucrose, 50 mmol/L GlcNAc and protease inhibitor cocktail (1:1,000, Sigma). First centrifugation was performed at 1,500 g for 15 min at 4° C. to spin down the crude nuclear fraction. The supernatant was spun at 8,000 g for 15 min at 4° C. and subsequently for 1 h at 160,000 g at 4° C. The final supernatant represented the cytosolic fraction. Whole heart tissue homogenate was prepared with 0.2 ml of lysis buffer (20 mmol/L Tris, pH 7.4, 20 mmol/L NaCl, 0.1 mmol/L EDTA, 1% Triton X-100, 0.5% sodium deoxycholate, 1 mmol/L dithiothreitol, 1 mmol/L β-glycerophosphate, 10 mmol/L Na-pyrophosphate, 50 mmol/L NaF, 1 mmol/L Na-ortho-vanadate, 50 mmol/L GlcNAc, proteinase inhibitor cocktail).

Twenty μg of protein was mixed with Laemmli sample buffer at room temperature for 10 min (samples for anti-O-GlcNAc antibody detection was heated at 70° C. for 10 min) and then loaded onto 4-10% gradient Tris/glycine gels. Separated proteins were transferred to nitrocellular membranes and blocked overnight with 3% BSA at 4° C. Blots were incubated with a primary antibody (1:5000 CTD 110.6 antibody, a gift by Dr. Gerald Hart, The Johns Hopkins University, Baltimore, Md.; 1:1000 polyclonal SERCA2a antibody, Affinity Bioreagents, Inc.; phospholamban antibody, phosphorylated phospholamban antibody, Upstate; α-actin antibody, Sigma; 1:1000 anti-OGT antibody, a gift by Dr. John A. Hanover, National Institutes of Health, MA) for 1 hour at room temperature, followed by a 1 hour incubation with a 1:5000 dilution of secondary antibody (anti-rabbit IgG-HRP conjugated, anti-rabbit IgG-HRP conjugated, anti-mouse IgM-HRP conjugated, anti-rabbit IgG-HRP conjugated, Sigma, respectively). Bands were visualized by reacting with chemiluminescent substrate (PerkinElmer Life Sciences) and exposed to film. Films were scanned and analyzed by IMAGE-J™ software (NIH).

OGT activity and GCA activity assay: The OGT activity assay was measured with the protein precipitated by 30% saturated ammonium sulfate from heart tissue extract as previously described, e.g., by Haltiwanger (1992) J. Biol. Chem. 267:9005-9013; Akimoto (2000) Diabetologia 43:1239-47. The peptide PGGSTPVSSANMM (SEQ ID NO:2) was used as a substrate. The OGT activity was expressed as dpm/ug protein.

Cytosolic fractions prepared as described above were used for GCA activity measurement (see also Dong (1996) J. Biol. Chem. 271:20845-52), except that 1 mM PMSF was added to the homogenization buffer but not GlcNAc and proteinase inhibitor cocktail. 50 mM GalNAc was added to inhibit lysosomal hexosaminidases. The activity was expressed as units/mg.

Statistic analysis: All data are presented as mean±SEM. One way ANOVA with appropriate post-hoc or unpaired Student t test was used for comparison between two groups with SPSS v9.0 software package. $P<0.05$ was considered to be statistically significant.

Results

General features of the experimental animals: All the diabetic mice used in this study had a blood glucose level >22 mmol/L at their time of sacrifice. As described previously by Trost (2002) supra, the diabetic mice studied here also had lower body weights (22.4±1.1 g vs 29.1±0.5 g, $P<0.01$) and higher blood glucose levels after STZ injection (40.6±2.6 mmol/L vs 9.5±0.5 mmol/L, $P<0.05$) than normal NIH Swiss mice. Diabetic mice were randomly divided into two groups: Dia+SR– group (mice receiving Adv-SR–) and Dia+GCA (mice receiving Adv-GCA). Before gene therapy, both body weights and blood glucose levels were comparable between these two groups (body weight: Dia+SR–, 22.2±1.3 g vs Dia+GCA, 22.6±1.0 g; blood glucose: Dia+SR–, 38.2±2.1 mmol/L vs Dia+GCA, 43.0±3.1 mmol/L; $P>0.05$), which indicated that mice in these two groups had a similar severity of diabetes. After gene therapy, no significant changes were observed in body weight or blood glucose level in both groups (P>0.05).

Figure 8:
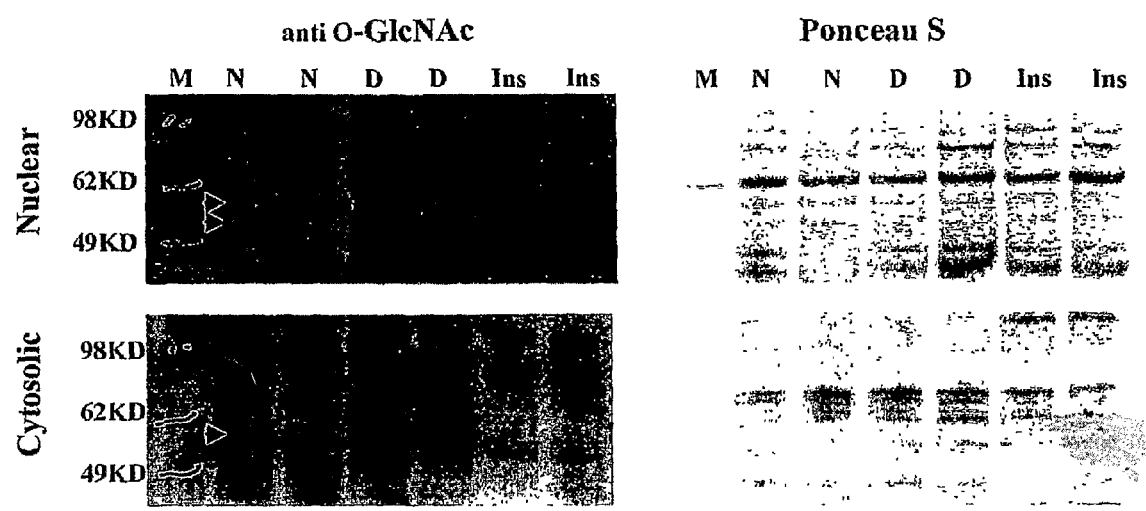
FIG. 8 illustrates O-GlcNAcylated proteins detected in nuclear fractions and cytosolic fractions isolated from diabetic hearts and normal hearts, as described in detail in Example 2, below.

Excessive O-GlcNAcylation of cellular proteins in STZ-induced diabetic hearts was directly confirmed by Western blot analysis with anti-O-GlcNAc antibody. As shown in FIG. 8, more O-GlcNAcylated proteins were detected in nuclear fractions (indicated by arrows) isolated from diabetic hearts than that from normal hearts. Similarly, more O-GlcNAcylated proteins were also detected in cytosolic fractions (indicated by arrows) isolated from diabetic hearts than that from normal hearts. Excess O-GlcNAcylation of cellular protein in diabetic hearts was prevented by insulin treatment.

FIG. 8 illustrates that overall cellular protein O-GlcNAc modification was more prominent in the STZ-induced type I diabetic heart (D) than in normal heart (C), which was significantly prevented by insulin treatment (Ins). The same blot was stained by Ponceau S or reacted with O-GlcNAc antibody. M indicates molecular markers. Arrows indicate proteins showing increased O-GlcNAcylation.

Figure 9:
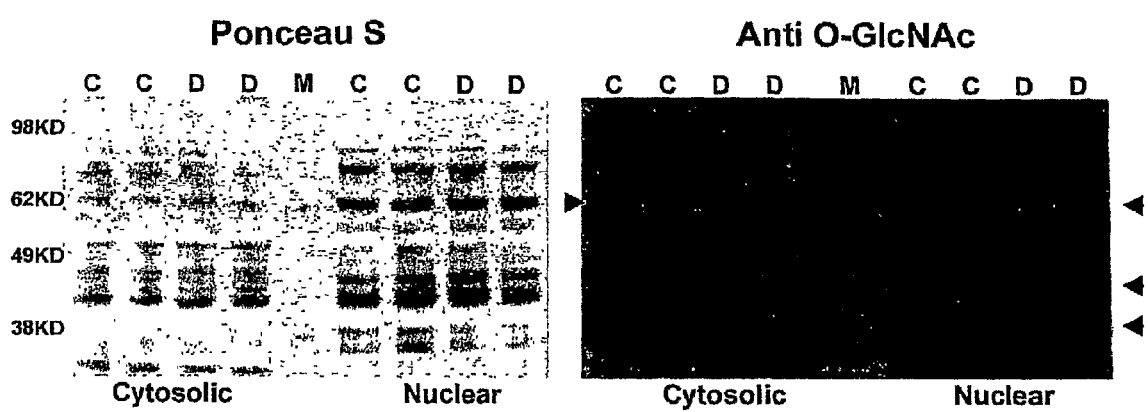
FIG. 9 illustrates overall cellular protein O-GlcNAc modification in polygenic type II diabetic hearts and in normal control hearts, as described in detail in Example 2, below.

Additionally, as shown in FIG. 9, similar excess cellular O-GlcNAcylation was also observed in the cytosolic and nuclear fraction from the polygenic type II diabetic hearts. FIG. 9 illustrates that overall cellular protein O-GlcNAc modification was more prominent in polygenic type II diabetic heart (D) than in normal control heart (C). The same blot was stained by Ponceau S or reacted with O-GlcNAc antibody. M indicates molecular markers. Arrows indicate proteins showing increased O-GlcNAcylation.

Figure 10:
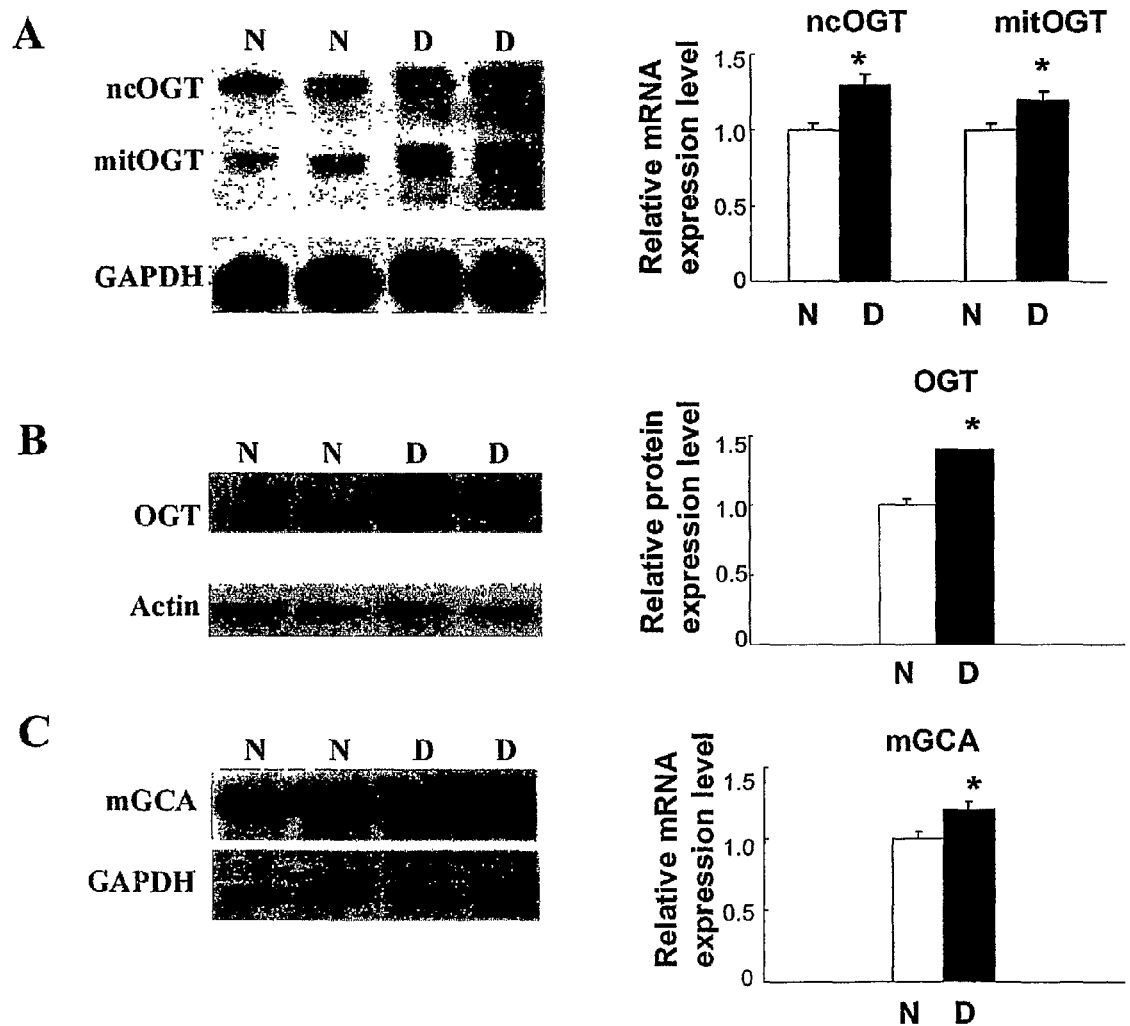
FIG. 10 illustrates mRNA expression level of both ncOGT and mitOGT isoform in the diabetic heart, as described in detail in Example 1, below.

In order to further understand excess O-GlcNAcylation in the diabetic heart, the expression levels and enzymatic activities of OGT and GCA were also determined. As shown in FIG. 10, the mRNA expression level of both ncOGT and mitOGT isoform was upregulated approximately 20-30% in the diabetic heart. The protein expression levels of OGT were increased approximately 30% in the diabetic heart. However, the OGT activity was not significantly changed in the diabetic heart relative to that in the normal heart (110.52±3.42 vs 96.51±9.29 dpm/ug, P>0.05). Additionally, the mRNA expression level of GCA was also increased approximately 30% in the diabetic heart. Similarly to the OGT enzymatic activity, the GCA activity was not increased in the diabetic heart (0.36±0.03 units/mg vs 0.39±0.04 units/mg, P>0.05).

FIG. 10 illustrates that mRNA and protein expression levels of OGT and GCA mRNA level were increased in the diabetic heart. FIG. 10A illustrates mRNA expression of OGT; FIG. 10B illustrates protein expression of OGT; FIG. 10C illustrates mRNA expression of mouse GCA (mGCA). Left panels: representative RNase protection assay or Western blot image; Right panels: relative mRNA or protein expression levels were represented as mean±SE. ncOGT: the nucleocytoplasmic isoform of OGT, mitOGT: the mitochondrial isoform of OGT. N: normal heart, D: diabetic heart. *P<0.05, compared with N.

Figure 11:
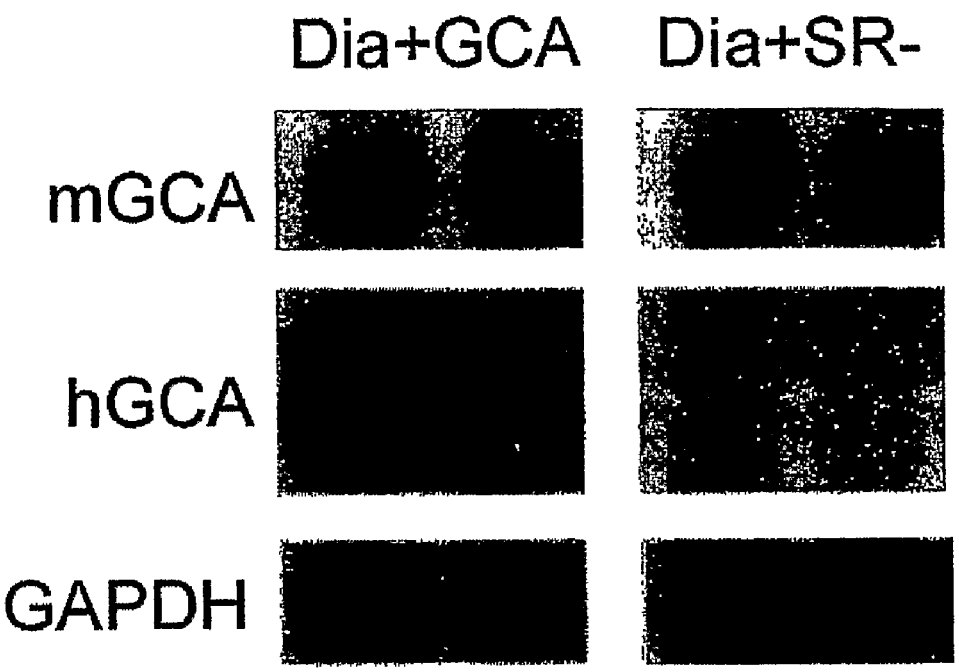
FIG. 11A illustrates RNase protection assay data confirming overexpression of GCA in diabetic hearts receiving Adv-GCA.
FIG. 11B illustrates data showing that the activity of GCA was higher in diabetic hearts receiving Adv-GCA (Dia+ GCA) than observed in diabetic hearts receiving Adv-SR- (Dia+SR-), as described in detail in Example 2, below.
Figure 11:
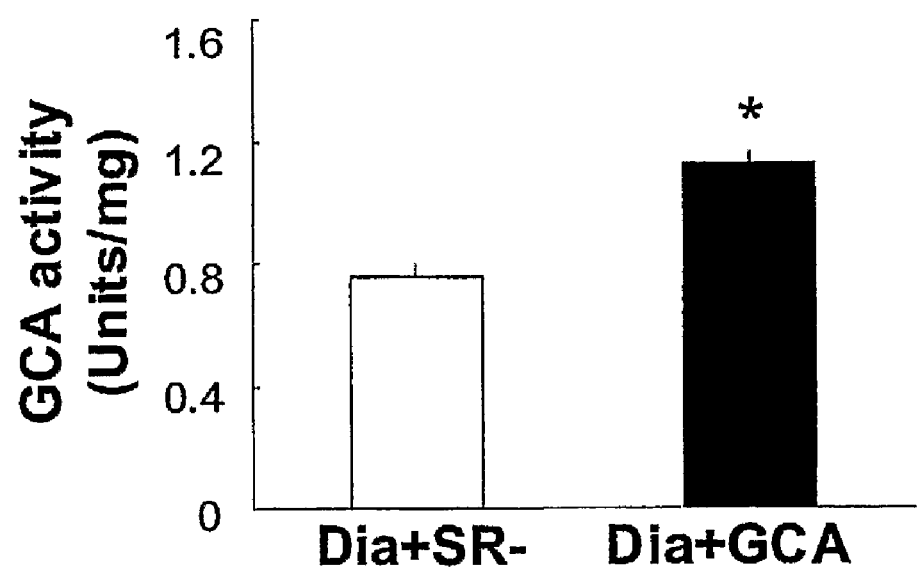

Confirming the overexpression of GCA in diabetic hearts after receiving in vivo adenoviral gene delivery: The overexpression of GCA mediated by adenovirus was confirmed by RNase protection assay with a human GCA (hGCA) specific probe. As shown in FIG. 11A, hGCA mRNA was well expressed in diabetic hearts 5 days after the Adv-GCA injection. The mRNA expression level of endogenous mouse GCA, detected by a second probe specific to mouse GCA sequence, was not affected by exogenous GCA overexpression. As shown in FIG. 11B, the overall GCA activity was increased approximately 50% in diabetic hearts receiving Adv-GCA gene therapy.

FIG. 11A illustrates RNase protection assay data confirming overexpression of GCA in diabetic hearts receiving Adv-GCA. hGCA: exogenous human GCA; mGCA: endogenous mouse GCA. FIG. 11B illustrates data showing that the activity of GCA was higher in diabetic hearts receiving Adv-GCA (Dia+GCA) than observed in diabetic hearts receiving Adv-SR− (Dia+SR−). * P<0.01, compared with Dia+SR−.

Figure 12:
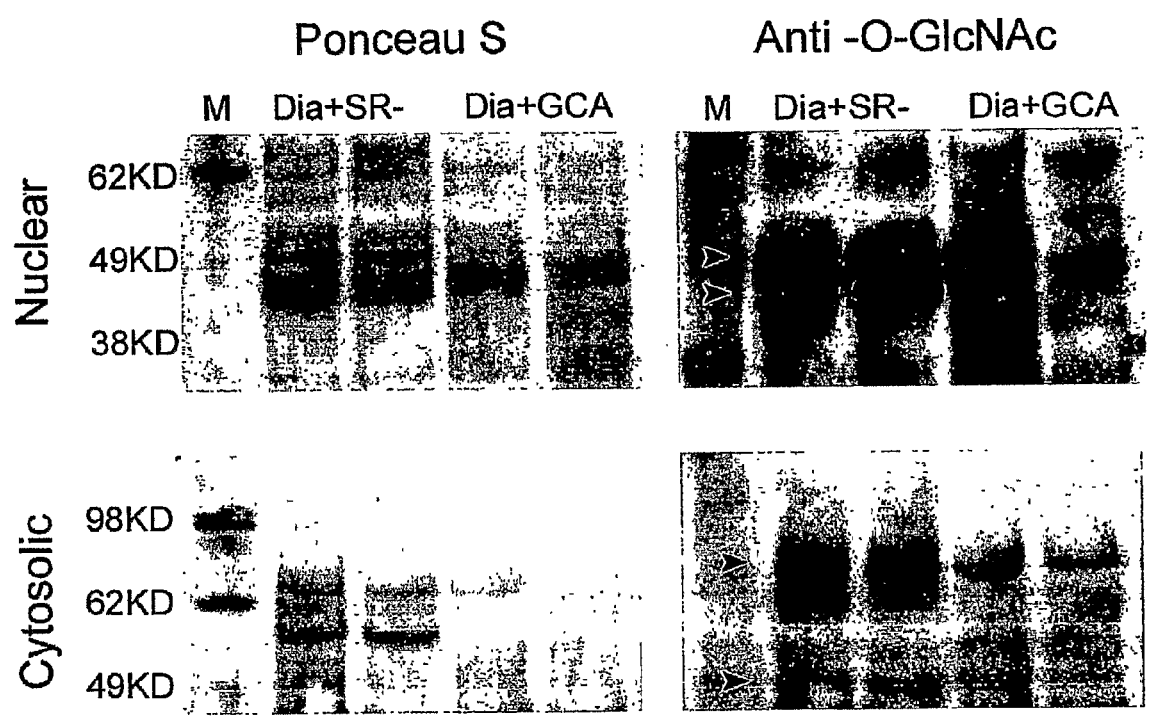
FIG. 12 illustrates overall cellular protein O-GlcNAc modification was reduced in diabetic hearts receiving Adv-GCA (Dia+GCA) in comparison with diabetic hearts receiving Adv-SR- (Dia+SR-), as described in detail in Example 2, below.

The reduction of cellular O-GlcNAcylation in diabetic hearts after GCA overexpression was further evaluated by Western blot using an O-GlcNAc antibody. Compared with diabetic hearts receiving Adv-SR−, O-GlcNAcylated proteins were less abundant in diabetic hearts receiving Adv-GCA treatment. FIG. 12 illustrates overall cellular protein O-GlcNAc modification was reduced in diabetic hearts receiving Adv-GCA (Dia+GCA) in comparison with diabetic hearts receiving Adv-SR− (Dia+SR−). The same blot was stained by Ponceau S or reacted with O-GlcNAc antibody. Arrows indicate proteins with altered O-GlcNAcylation. As shown in FIG. 12, a reduction in overall cellular O-GlcNAcylation was observed both in nuclear (indicated by arrows) and cytosolic fraction (indicated by arrows) from Dia+GCA group in comparison with those from Dia+SR− group. The overall reduction appeared more prominent in the nuclear fraction.

Figure 13:
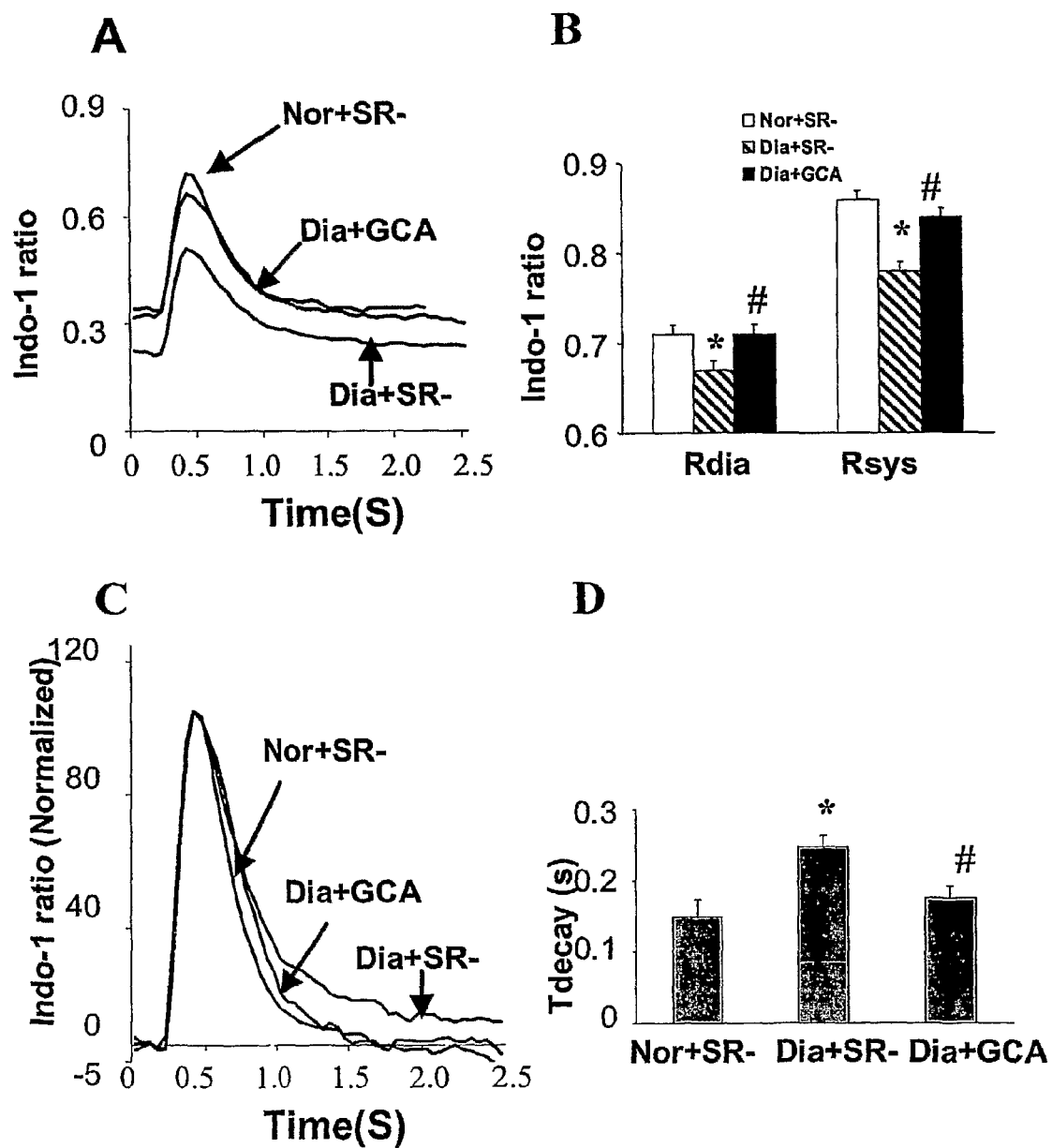
FIG. 13 illustrates data showing the effects of overexpressing GCA on $Ca^{2+}$ transient in diabetic cardiac myocytes.

Effects of overexpression of GCA on $Ca^{2+}$ transients in diabetic cardiac myocytes: The effects of overexpression of GCA on $Ca^{2+}$ transients were studied by directly co-injecting Adv-GCA and Adv-GFP into the hearts of diabetic mice 2 weeks after STZ induction. Cardiac myocytes were isolated after 5 days and only GFP positive cells were analyzed. FIG. 13 illustrates data showing the effects of overexpressing GCA on $Ca^{2+}$ transient in diabetic cardiac myocytes. (FIG. 13A) Panel A: averaged $Ca^{2+}$ transient; (FIG. 13B) Panel B: comparison of diastolic indo-1 ratio (Rdia), systolic indo-1 ratio (Rsys); (FIG. 13C) Panel C: averaged normalized $Ca^{2+}$ transient; (FIG. 13D) Panel D: comparison of diastolic decay time ($T_{decay}$). Nor+SR−, normal mice receiving Adv-SR−; Dia+GCA, diabetic mice receiving Adv-GCA; Dia+SR−, diabetic mice receiving Adv-SR−. *P<0.01, compared with Nor+SR−; #P<0.01 compared with Dia+SR−.

As shown in FIG. 13 (panels A, B), cardiac myocytes from Dia+SR− group (n=80) exhibited significantly lower systolic and diastolic calcium concentration, as indicated by lower basal and peak indo-1 ratios (Rdia and Rsys) compared to cells isolated from Nor+SR− group (n=98) (Rdia: Dia+SR−, 0.67±0.01 vs Nor+SR−, 0.71+/−0.01; Rsys: Dia+SR− 0.78±0.01 vs Nor+SR−, 0.86±0.01; P<0.01). In addition, the diastolic $T_{decay}$ was prolonged approximately 40% in myocytes from Dia+SR− in comparison with that in normal myocytes from Nor+SR−group (0.25±0.02s vs 0.15±0.01s; P<0.01) (FIGS. 13C, 13D). These results indicate that calcium handling in diabetic cardiomyocytes was significantly impaired in STZ-induced diabetic hearts.

The beneficial effects of overexpressing GCA on $Ca^{2+}$ transients in diabetic cardiac myocytes are also shown in FIG. 13. Compared with myocytes from the Dia+SR− group, myocytes from the Dia+GCA group (n=104) had higher diastolic and systolic indo-1 ratio (Rdia 0.71±0.01 vs 0.67±0.01; Rsys 0.84±0.01 vs 0.78±0.01; P<0.01). The diastolic $Ca^{2+}$ $T_{decay}$ in diabetic myocytes from Dia+GCA group was significantly shorter than that in those from Dia+SR− group (0.18±0.01s vs 0.15±0.01s; P<0.0.1). All these three parameters were altered towards similar level as observed in myocytes from Nor+SR− group (P>0.05).

To further evaluate the effects of Adv-GCA on calcium handling, sarcoplasmic reticulum $Ca^{2+}$ load was measured as caffeine-induced $Ca^{2+}$ release in these myocytes. Sarcoplasmic reticulum $Ca^{2+}$ load was approximately 33% lower than normal in control diabetic myocytes from Dia+SR− group (0.14±0.01 vs 0.21±0.01; P<0.01). However, sarcoplasmic reticulum $Ca^{2+}$ load was significantly increased 28% in cardiac myocytes from Dia+GCA group (0.18±0.02 vs 0.14±0.01; P<0.05).

We also examined the effects of Adv-GCA on $Ca^{2+}$ transient in normal myocytes. Our measurements indicated that Rdia was higher (P<0.05) in myocytes isolated from normal hearts receiving Adv-GCA than those receiving Adv-SR−. Rsys and $T_{decay}$ were not changed in normal myocytes receiving Adv-GCA.

Effects of overexpression of GCA on contractile function in diabetic cardiac myocytes: To evaluate the effects of overexpression of GCA on contractile function, isolated cardiac myocytes were analyzed with edge-detection technique. As shown in Table 1, below, cardiac myocytes from Dia+SR− group manifested prominent contractile dysfunction, represented by a 48% reduction in fractional shortening (P<0.01) and a 53% reduction in +dL/dt (P<0.01) as well as 59% reduction in −dL/dt (P<0.01), compared with myocytes from Nor+SR− group.

TABLE 1

Effects of overexpression of GCA on contractile function in diabetic cardiac myocytes:

| | Cell length (μm) | FS (%) | +dL/dt (μm/s) | −dL/dt (μm/s) |
|---|---|---|---|---|
| Nor+SR− (n = 33) | 118 ± 3 | 12.05 ± 1.16 | 168 ± 9 | 137 ± 7 |
| Dia+SR− (n = 30) | 115 ± 7 | 6.20 ± 1.17* | 84 ± 12* | 55 ± 10* |
| Dia+GCA (n = 30) | 109 ± 6 | 10.77 ± 1.64# | 151 ± 26# | 103 ± 15#§ |

FS: fractional shortening;
Nor+SR−: normal heart receiving Adv−SR−,
Dia+SR−: Diabetic heart receiving Adv−SR−,
Dia+GCA: diabetic heart receiving Adv−GCA;
*P < 0.01,
§P < 0.05 compared with Nor+SR−;
P < 0.01 compared with Dia+SR−.

As shown in Table 1, cardiac myocytes from Dia+GCA group manifested significantly improved contractile function. Compared with those from Dia+SR− group, myocytes from Dia+GCA group had 74% increase in fractional shortening (P<0.01), 79% increase in +dL/dt (P<0.01) and 85% increase in −dL/dt (P<0.01). Both fractional shortening and +dL/dt in myocytes from Dia+GCA group were recovered towards normal (P>0.05). However, there was still 25% decrease in −dL/dt of these myocytes, compared with those from Nor+SR− group (p<0.05).

Effects of overexpression of GCA on contractile function in the intact diabetic heart: We reported previously an approximately 30% decrease in contractile function in isolated perfused hearts with STZ-induced diabetes, see Trost (2002) supra. Because the enzymatic isolation of individual myocytes can be a selective process, involving the survival of only the healthiest myocytes, we sought to confirm our observations by examining contractile function in the whole heart. In this study, STZ-induced diabetic hearts receiving Adv-SR− (n=6) exhibited 27% and 21% reduction in −dP/dt and developed pressure (DP) respectively in comparison with normal control hearts (n=9) (−dP/dt: 2296+/−120 mmHg/S vs 3138+/−259 mmHg/S; DP: 90+/−5 mmHg vs 114+/−8 mmHg; P<0.05). However, the diabetic hearts receiving Adv-GCA (n=7) had a significant 15% increase in −dP/dt and DP relative to the diabetic hearts receiving Adv-SR− (−dP/dt: 2629+/−63 mmHg/S vs 2296+/−120 mmHg/S; DP: 104+/−2 mmHg vs 90+/−5 mmHg; P<0.05). There was no significant difference in +dP/dt either between normal and the diabetic hearts or between diabetic hearts receiving Adv-SR− and diabetic hearts receiving Adv-GCA (P>0.05). These data demonstrated that overexpression of GCA in the diabetic heart had beneficial effects on its global contractility.

Figure 14:
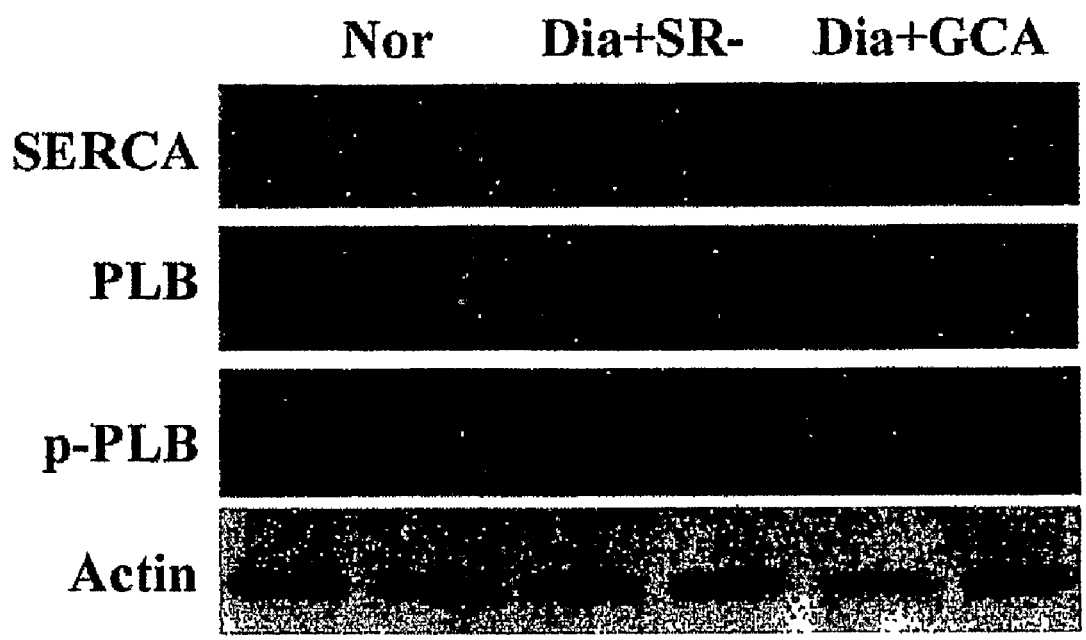
FIG. 14 illustrates data showing alterations of protein expression in diabetic hearts receiving Adv-GCA gene delivery, as described in detail in Example 2, below.
Figure 14:
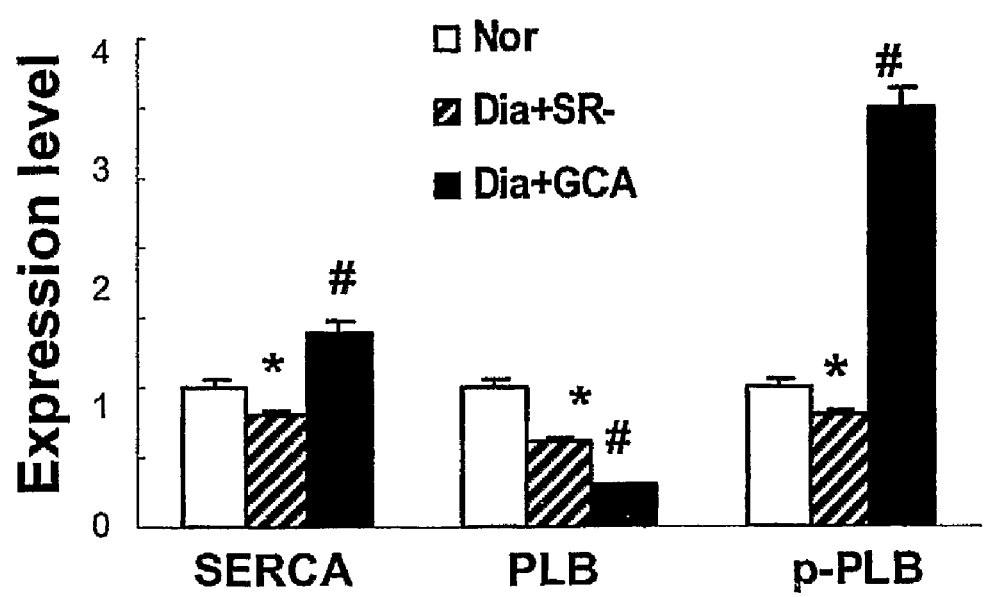

Effects of overexpression of GCA on sarcoplasmic reticulum $Ca^{2+}$ regulating protein: To understand the mechanism of the beneficial effects of GCA overexpression on the diabetic heart, protein expression levels of SERCA2a, phospholamban (PLB) and phosphorylated PLB (p-PLB) were examined. The data illustrated in FIG. 14 shows alterations of protein expression in diabetic hearts receiving Adv-GCA gene delivery. As shown in FIG. 14, the expression levels of SERCA, PLB, p-PLB were all significantly reduced in diabetic hearts. Compared with the expression in Dia+SR− group, SERCA2a expression was increased about 40%, while PLB protein expression was reduced about 50% in hearts from Dia+GCA group. Furthermore, the percentage of p-PLB from PLB was increased about 2 folds in diabetic hearts from Dia+GCA group in comparison with Dia+SR− group. In FIG. 14, whole cell extract was made from normal heart or diabetic hearts receiving either Adv-SR− (Dia+SR−) or Adv-GCA (Dia+GCA). SERCA and PLB expression level (pentamer form) were adjusted by actin and p-PLB level was adjusted by PLB. Upper panel: representative Western blot image; Lower panel: relative expression level was represented as mean±SE. *P<0.05, compared with normal; #P<0.05, compared with Dia+SR−.

Discussion

These investigations demonstrate for the first time that excess protein O-GlcNAcylation occurs in vivo in the diabetic heart, and that a reduction of excessive O-GlcNAc modification by overexpressing an adenovirus encoded O-GlcNAcase enzyme in the heart has beneficial effects on cardiac function in STZ-induced diabetes.

We observed, through protein analyses, that diabetic hearts exhibited excessive O-GlcNAcylation in both type I and type II diabetes. This is similar to what has been observed in other tissues in diabetic animals and diabetic patients; see, e.g., Akimoto (2003) Invest. Opthalmol. Vis. Sci. 2003; 44:3802-9; Akimoto (2000) supra. Although both mRNA and protein expression levels of OGT were upregulated in the STZ-induced diabetic heart, the enzymatic activity of OGT did not increase with protein amount. This finding is in agreement with previous observations (e.g., Akimoto (2000) supra; Kreppel (1997) J. Biol. Chem. 272:9308-9315), indicating that additional factors may regulate the activity of OGT (see, e.g., Kreppel (1999) J. Biol. Chem. 274:32015-3222.

Additionally, unlike the increase in OGT activity observed in pancreas from STZ-induced diabetic rats, there was no significant change in enzymatic activity in hearts from STZ-induced diabetic mice. Thus it is suggested that OGT activity is modulated differentially in different types of tissue. Our previous studies have shown that the intracellular UDP-GlcNAc levels are significantly elevated in the diabetic heart in comparison with normal heart (see, e.g., Clark (2003) J. Biol. Chem. 278:44230-44237. It is likely that excess substrate supply, derived from the enhanced hyperglycemia-driven hexosamine pathway flux, rather than altered enzymatic activity leads to increased protein O-GlcNAc modification in the STZ-induced diabetic heart.

O-GlcNAcase has been characterized as an enzyme specific for O-GlcNAc removal (see, e.g., Dong (1994) J. Biol. Chem. 269:19321-19330; Gao (2001) J. Biol. Chem. 276:

9838-9845) and the adenovirus-mediated overexpression of GCA has been used successfully in our lab to reduce O-GlcNAcylation in high glucose- or glucosamine-treated neonatal cardiac myocytes (see Clark (2003) supra). Although no significant GCA enzymatic change is detected in the diabetic heart, the present study demonstrates that overexpressing O-GlcNAcase in vivo using exemplary methods and compositions of the invention is able to increase O-GlcNAcase activity approximately 50% and is effective at reducing cellular O-GlcNAcylation levels in the heart. A reduction in cellular O-GlcNAcylation was observed both in cytosolic and nuclear fractions, suggesting that GCA overexpression may have diverse effects on cellular function.

This study also demonstrated that overexpression of GCA using exemplary methods and compositions of the invention has a beneficial effect on cardiac function in diabetes. The results presented here demonstrate that overexpression of GCA could dramatically improve calcium cycling in diabetic myocytes by enhancing the $Ca^{2+}$ transient and sarcoplasmic reticulum $Ca^{2+}$ loading. In the STZ-induced diabetic heart, decreased SERCA expression level and phosphorylation of PLB explain the cardiac dysfunction observed in these diabetic hearts. The alterations in sarcoplasmic reticulum protein expression observed after GCA overexpression further provide an explanation for these changes in calcium cycling. The higher SERCA2a expression and lower PLB expression in diabetic hearts following Adv-GCA delivery increased the SERCA2a/PLB ratio and SERCA2a activity, which mirrors the observed normalization of calcium transients and increases in sarcoplasmic reticulum calcium load. The improvement in calcium cycling (in practicing the methods of the invention) can certainly contribute to the enhancement of contractility in diabetic myocytes by overexpressing GCA. The improvement in calcium cycling (in practicing the methods of the invention) further facilitates the global functional improvement observed in the diabetic heart. However, unlike the restoration of contractile function observed in diabetic hearts treated with insulin, contractile function increased only 15% in isolated perfused hearts overexpressing GCA. Other factors unrelated to O-GlcNAcylation, such as non-enzymatic glycation of SERCA2a (see, e.g., Bidasee (2004) Diabetes 53:463-473), may also play a role in diabetic cardiac dysfunction.

There is compelling evidence indicating that O-GlcNAcylation involves regulation of gene transcription, protein synthesis and degradation (see, e.g., Vosseller (2002) Curr. Opin. Chem. Biol. 6:851-857). A series of studies have established a role of O-GlcNAc in suppressing transcription through modifying RNA polymerase II (see, e.g., Comer (2001) Biochemistry 40:7845-7852), Sp1 (see, e.g., Roos (1997) Mol Cell Biol. 17:6472-6480; Yang (2001) Proc. Natl. Acad. Sci. USA 98:6611-6616), and histone deacetylase (see, e.g., Yang (2002) Cell 110:69-80).

We have previously shown that SERCA2a promoter activity negatively corresponds with the amount of O-GlcNAcylation on Sp1 in cardiac myocytes (see, e.g., Clark (2003) supra). Therefore, it is likely that the increased SERCA2a expression observed in diabetic hearts receiving Adv-GCA results from a decrease in Sp1 O-GlcNAcylation via GCA overexpression. However, another series of studies suggest a positive role of O-GlcNAc in up-regulating transcriptional events, including those specifically responsive to glucose (see, e.g., James (2002) Diabetes 51:1146-1156; Fiordaliso (2001) Diabetes 50:2363-2375). Additionally, O-GlcNAc modification has been demonstrated to inhibit the proteasome (see, e.g., Zhang (2003) Cell 115:715-725; Liu (2004) J. Neurochem. 89:1044-1055; Han (1997) Mol Cell Biol. 17:2550-2558) and stabilize certain proteins. Noting that the invention is not limited by any particular mechanism of action, we postulate that different mechanisms may contribute to the down regulation of PLB observed in diabetic heart receiving Adv-GCA delivery.

The study described herein also demonstrated an increased phosphorylated PLB in diabetic heart overexpressing GCA. This provides another explanation for enhanced SERCA2a function following GCA gene delivery, as it has been shown that the phosphorylation of PLB promotes oligomerization of PLB and decreases its inhibitory effects on SERCA2a (see, e.g., Reddy (1999) Biochemistry 38:3954-62; Li (1999) Biophys J. 76:2587-99; Cornea (1997) Biochemistry. 36:2960-2967; Frank (2000) Ann Med. 32:572-578; Colyer (1998) Ann. NY Acad. Sci. 853:79-91). Reciprocal phosphorylation and O-GlcNAcylation occurring at the same amino acid site have been identified in several proteins, including Tau and RNA polymerase II. We have determined that PLB could be immunoprecipitated with anti-O-GlcNAc antibody (CTD 110.6) from cardiac myocytes cultured with high glucosamine and adenovirus expressing OGT.

In summary, this study demonstrates that excessive cellular O-GlcNAcylation exists in the diabetic heart, and that practicing the methods and compositions of the invention can reduce excess O-GlcNAcylation by overexpressing GCA; and practicing the methods and compositions of the invention can also have beneficial effects on calcium handling and diabetic cardiac function. This study also demonstrates that overexpressing GCA, e.g., as mediated by a expression construct—an adenovirus—provides an effective therapeutic means to ameliorate diabetic cardiomyopathy.

A number of embodiments of the invention have been described. Nevertheless, it will be understood that various modifications may be made without departing from the spirit and scope of the invention. Accordingly, other embodiments are within the scope of the following claims.

What is claimed is:

1. A method for normalizing or improving calcium cycling in a myocyte under hyperglycemic or diabetic conditions, or a diabetic heart, by enhancing the $Ca^{2+}$ transient and sarcoplasmic reticulum $Ca^{2+}$ loading, the method comprising increasing O-GlcNAcase (GCA) enzyme levels and activity in the myocyte by
   (a) providing a nucleic acid encoding an O-GlcNAcase (GCA) enzyme, wherein the nucleic acid is operatively linked to a promoter constitutively or inducibly active in the myocyte or the heart; and
   (b) directly administering an effective amount of the O-GlcNAcase (GCA)-encoding nucleic acid to the myocyte or heart, and inducing expression of the O-GlcNAcase-encoding nucleic acid if the promoter is an inducible promoter, thereby expressing an O-GlcNAcase (GCA) enzyme in the myocyte to reduce excess O-GlcNAcylation and enhance $Ca^{2+}$ transient and sarcoplasmic reticulum $Ca^{2+}$ loading in the myocyte or the diabetic heart.

2. The method of claim 1, wherein an effective amount of the O-GlcNAcase (GCA)-encoding nucleic acid is administered to the diabetic myocyte ex vivo.

3. The method of claim 1, wherein the hyperglycemic or diabetic conditions, or diabetic heart, is caused by type I diabetes or type II diabetes.

4. The method of claim 1, wherein administering the effective amount of the GCA-encoding nucleic acid causes reduction of excessive O-GlcNAcylation in cytosolic and/or nuclear proteins.

5. The method of claim 1, wherein a GCA-encoding nucleic acid is contained within a cloning vehicle, an expression cassette or vector.

6. The method of claim 5, wherein the cloning vehicle, expression cassette or vector comprises a viral vector, a plasmid, a phage, a phagemid, a cosmid, a fosmid, a bacteriophage or an artificial chromosome.

7. The method of claim 1, wherein the viral vector comprises an adenovirus vector, a retroviral vector or an adeno-associated viral vector.

8. The method of claim 7, wherein the retroviral vector is a lentiviral vector.

9. An in vitro method for normalizing or improving calcium cycling in a myocyte under hyperglycemic or diabetic conditions, the method comprising increasing O-GlcNAcase (GCA) enzyme levels and activity in the myocyte by:
   (a) providing a nucleic acid encoding an O-GlcNAcase (GCA) enzyme, wherein the nucleic acid is operatively linked to a promoter constitutively or inducibly active in the myocyte; and
   (b) directly administering an effective amount of the O-GlcNAcase (GCA)-encoding nucleic acid to the myocyte, and inducing expression of the O-GlcNAcase -encoding nucleic acid if the promoter is an inducible promoter, thereby expressing an O-GlcNAcase (GCA) enzyme in the myocyte to reduce excess O-GlcNAcylation and enhance $Ca^{2+}$ transient and sarcoplasmic reticulum $Ca^{2+}$ loading in the myocyte.

10. The method of claim 1, wherein an effective amount of the O-GlcNAcase (GCA)-encoding nucleic acid is administered to the heart ex vivo.

* * * * *